United States Patent [19]

Murase et al.

[11] Patent Number: 4,618,627
[45] Date of Patent: Oct. 21, 1986

[54] CATECHOL DERIVATIVES AND PHARMACEUTICAL COMPOSITIONS THEREOF FOR INHIBITING ANAPHYLAXIS (SRS-A)

[75] Inventors: Kiyoshi Murase, Saitama; Toshiyasu Mase, Chiba; Hideki Arima, Tokyo; Kenichi Tomioka, Saitama, all of Japan

[73] Assignee: Yamanouchi Pharmaceutical Co., Ltd., Tokyo, Japan

[21] Appl. No.: 609,143

[22] Filed: May 11, 1984

[30] Foreign Application Priority Data

May 13, 1983 [JP] Japan ................................ 58-83748
Oct. 25, 1983 [JP] Japan ................................ 58-199854
Dec. 29, 1983 [JP] Japan ................................ 58-248034
Feb. 24, 1984 [JP] Japan ................................ 59-34979

[51] Int. Cl.⁴ ............... C07C 39/08; C07C 43/164; C07C 47/11; A61K 31/05
[52] U.S. Cl. .................................. 514/678; 514/718; 514/731; 514/699; 568/763; 568/765; 568/308; 568/766; 568/652; 568/329; 568/731; 568/442; 568/647; 568/649; 568/660; 568/662
[58] Field of Search ............... 568/308, 766, 652, 763, 568/765, 329, 731, 442, 647, 649, 660, 662; 514/699, 678, 718, 731

[56] References Cited

U.S. PATENT DOCUMENTS

| 1,306,710 | 6/1919 | Nomura | 568/308 |
| 3,256,336 | 6/1966 | Lange | 568/766 X |
| 4,062,978 | 12/1977 | Cole et al. | 568/766 X |

FOREIGN PATENT DOCUMENTS 2349537  4/1974  Fed. Rep. of Germany ...... 568/308

OTHER PUBLICATIONS

Pepper et al., Canadien Jour. Chem., vol. 49, No. 20, (1971), 3394–3395.

Primary Examiner—Bernard Helfin
Attorney, Agent, or Firm—Burgess, Ryan & Wayne

[57] ABSTRACT

A catechol derivative represented by the formula

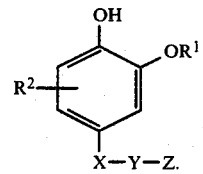

The compounds of this invention are useful for the prophylaxis and treatment for various allergic diseases, ischemic heart diseases and inflammations caused by slow reacting substance of anaphylaxis (SRS-A), since the compounds inhibit very potently the formation and release of SRS-A.

19 Claims, No Drawings

CATECHOL DERIVATIVES AND PHARMACEUTICAL COMPOSITIONS THEREOF FOR INHIBITING ANAPHYLAXIS (SRS-A)

FIELD OF THE INVENTION

This invention relates to novel catechol derivatives useful for medicaments and intermediates thereof.

BACKGROUND OF THE INVENTION

It is generally considered that in allergic asthma and other atopic diseases of man or anaphylactic shock in animals, several chemical mediators are released from the lung and other tissues cause troubles in living bodies, such as the constriction of smooth muscles, e.g., bronchi, pulmonary artery, etc., and the enhancement of vascular permeability in the skin. As such chemical mediators, there are histamine and SRS-A (slow reacting substance of anaphylaxis). Histamine plays an important role in guinea pig anaphylactic shock but not in allergic asthma in man (Eiser, "Pharmac. Ther.", 17, 239–250(1982)), whereas a number of lines evidence suggest that SRS-A is the most important chemical mediator of allergic asthma in man (Brocklehurst, "J. Physiol.", 151, 416–435(1960); Austen and Orange, "Am. Rev. Resp. Dis.", 12, 423–436(1975); Adams and Lichtenstein, "J. Immunol.", 122, 555–562(1979)).

The development of the medicaments for the prophylaxis, elimination, and reduction of immediate hypersensitivity reactions was performed aiming at inhibiting the production and release of such chemical mediators or antagonizing the action of these chemical mediators. As an inhibitor of histamine release, disodium cromoglycate (DSCG) is well known and as an inhibitor of actions induced by histamine, various anti-histamics are commercially available. On the other hand, SRS-A is known as a slow reactive and long acting chemical mediator while histamine is a rapid acting and short acting chemical mediator, and it has recently been recognized that SRS-A is a mixture of Leukotriens $C_4$, $D_4$ and $E_4$ the structures of which have been clarified by Dr. Samuelsson. SRS-A, i.e., Leukotriens are lipoxigenase products of polyunsaturated fatty acids (in particular, arachidonic acid) and it has been reported that SRS-A has various activities such as enhancement of mucus production, reduction of mucociliary transport, coronary artery constrictor action, reduction of cardiac contractility, etc., in addition to the actions in the above-described allergic reactions. Only a few materials have been known as the medicaments for inhibiting the production and release of SRS-A or the medicaments antagonizing these actions of SRS-A and they have not yet been clinically used.

As the result of various investigations on finding medicaments capable of inhibiting the production and release of SRS-A or medicaments capable of antagonizing the actions of SRS-A, the inventors have discovered that the compounds of this invention as described hereinafter are useful as medicaments capable of very strongly inhibiting the formation and release of SRS-A and/or medicaments capable of antagonizing the actions of SRS-A and the present invention has been attained based on the discovery.

SUMMARY OF THE INVENTION

The invention is a catechol derivative represented by the general formula (I)

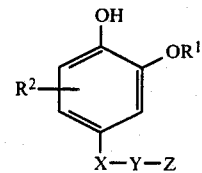

wherein $R^1$ represents a hydrogen atom or a lower alkyl group; $R^2$ represents a hydrogen atom or a halogen atom; X represents a straight chain or branched alkylene group having 1 to 15 carbon atoms or a vinylene group; Y represents a carbonyl group or a group shown by the formula

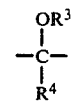

(wherein $R^3$ and $R^4$, which may be the same or different, each represents a hydrogen atom or a lower alkyl group); and Z represents a hydrogen atom, a straight chain or branched alkyl group having 1 to 15 carbon atoms or cycloalkyl; the sum of the carbon atoms of said X and Z being at least 3.

DETAILED DESCRIPTION OF THE INVENTION

Now, the "lower alkyl group" shown by $R^1$, $R^3$ and $R^4$ in the above-described general formula is a straight chain or branched alkyl group having 1 to 5 carbon atoms, such as a methyl group, an ethyl group, a propyl group, an isopropyl group, a butyl group, a pentyl group, etc.

The "halogen atom" shown by $R^2$ in the foregoing general formula includes a chlorine atom, a bromine atom, an iodine atom and a fluorine atom.

The "straight chain alkylene group" shown by X includes a methylene group, an ethylene group, a propylene group, a pentanylene group (or pentamethylene group, $-(CH_2)_5-$), a hexanylene group (hexamethylene group, $-(CH_2)_6-$), a heptanylene group (heptamethylene group, $-(CH_2)_7-$), a nonanylene group (nonamethylene group, $-(CH_2)_9-$), an undecanylene group (undecamethylene group, $-(CH_2)_{11}-$), a tridecamethylene group (tridecamethylene group, $-(CH_2)_{13}-$), a tetradecanylene group (tetradecamethylene group, $-(CH_2)_{14}-$), a pentadecanylene group (pentadecamethylene group, $-(CH_2)_{15}-$), etc. Also, the "branched alkylene group" shown by X includes the abovedescribed straight chain alkyl groups having a lower alkyl group of 1 to 5 carbon atoms at the optional position thereof. Specific examples of the branched alkylene group are a propylene group

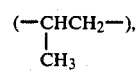

an ethylethylene group

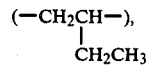

etc.

Examples of the group shown by

represented by Y in the foregoing general formula are a hydroxymethylene group, a methoxymethylene group, a methylhydroxymethylene group

a methylmethoxymethylene group

an ethylhydroxymethylene group

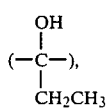

etc.

The "straight chain alkyl group" shown by Z in the foregoing general formula includes a propyl group, a pentyl group, a hexyl group, an octyl group, a nonyl group, a decyl group, an undecyl group, etc. Also, the "branched alkyl group" shown by Z includes alkyl groups having a lower alkyl group of 1 to 5 carbon atoms at an optional position thereof and specific examples are an isopropyl group, an isobutyl group, a 1-methylhexyl group, a 1-ethylpentyl group, a 1,5-dimethylhexyl group, a 2,3,5-trimethylheptyl group, a 4-propylnonyl group, a 1-hexylpeptyl group, etc. Also, the "cycloalkyl group" shown by Z includes a cyclopentyl group, a cyclohexyl group, etc.

When X represents a branched alkylene group, Y represents the group shown by

and or Z represents a branched alkyl group, which has different alkyl groups on a branched carbon atom, the compounds of this invention shown by the above-described general formula has at least one asymmetric carbon atom. Thus, the desired compounds of this invention include each separated steroisomer based on the asymmetric carbon atom and a mixture of these steroisomers.

Since the compounds of this invention shown by general formula (I) inhibit very potently the formation and release of SRS-A, the compounds are useful for the prophylaxis and treatment for various allergic diseases (e.g., bronchial asthma, allergic rhinitis, and urticaria) and ischemic heart diseases and inflamations caused by SRS-A.

PHARMACOLOGICAL EXPERIMENT (A) Passive peritoneal anaphylaxis (PPA) in rats

The method was based on that of Orange et al[1]. Briefly, male Wistar rats weighing 275 to 325 g (Shizuoka Exp. Animal Agric, Coop. Assoc.) were sensitized by intraperitoneally (i.p.) injecting 5 ml of diluted (40-fold) mouse anti-DNP reaginic serum (PCA titer: 1280). After 4 hr, 5 ml of Tyrode solution containing 250 μg heparin and 2 mg DNP-BSA was injected i.p. Test drugs (100 μg/kg) were dissolved in 0.6 ml of saline and injected i.p. 30 sec before antigen administration. Five min. later, the rats were decapitated and the peritoneal fluid was collected by opening the peritoneal cavity into polycarbonate tubes in ice. The supernatant was separated for bioassay from the cellular residue by centrifugation at 2000 rpm for 5 min at 4° C.

(1) Orange et al (1970) J. Immunol. 105, 1087-1095.

Histamine and SRS-A were assayed using isolated guinea-pig ileum in the presence of $10^{-7}$M FPL-55712 and $10^{-6}$M mepyramine, respectively, in addition to $5\times10^{-7}$M atropine. One unit of SRS-A refers to the concentration required to produce a contraction of the guinea-pig ileum equal in amplitude to that produced by 5 ng histamine base in that assay.

TABLE 1

| ALT-No | Example | Drug Formula | Rat PPA (100 μg/kg i.p.) Inhibition (%) | |
|---|---|---|---|---|
| | | | Histamine | SRS-A |
| — | — | (DSCG) | 75.2[1] | 46.6[1] |
| 18 | 1 | OH, OH, CH₂CH₂CHCH(CH₂)₃CH₃ / OH CH₃ | 37.8 | 76.6 |

TABLE 1-continued
| ALT-No | Example | Drug Formula | Rat PPA (100 μg/kg i.p.) Inhibition (%) | |
|---|---|---|---|---|
| | | | Histamine | SRS-A |
| 28 | 2 | 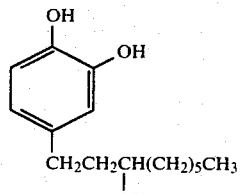 3,4-dihydroxyphenyl-CH₂CH₂CH(OH)(CH₂)₅CH₃ | 5.2 | 57.3 |
| 27 | 3 | 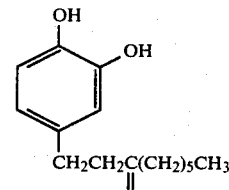 3,4-dihydroxyphenyl-CH₂CH₂C(O)(CH₂)₅CH₃ | 22.6 | 53.9 |
| 70 | 9 | 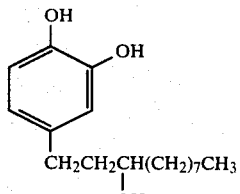 3,4-dihydroxyphenyl-CH₂CH₂CH(OH)(CH₂)₇CH₃ | 21.6 | 53.6 |
| 69 | 11 | 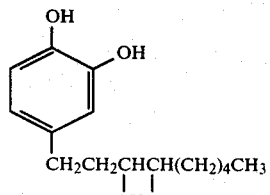 3,4-dihydroxyphenyl-CH₂CH₂CH(OH)CH(OCH₃)(CH₂)₄CH₃ | 17.6 | 66.6 |
| 82 | 14 | 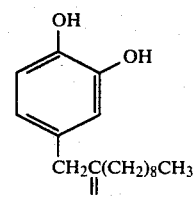 3,4-dihydroxyphenyl-CH₂C(O)(CH₂)₈CH₃ | 32.7 | 58.9 |
| 52 | 15 | 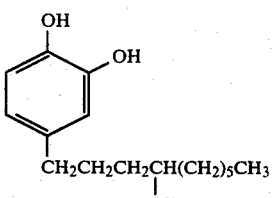 3,4-dihydroxyphenyl-CH₂CH₂CH₂CH(OH)(CH₂)₅CH₃ | 18.4 | 46.2 |
| 103 | 20 | 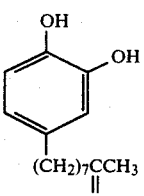 3,4-dihydroxyphenyl-(CH₂)₇C(O)CH₃ | 17.9 | 62.8 |

TABLE 1-continued

| ALT-No | Example | Drug Formula | Rat PPA (100 μg/kg i.p.) Inhibition (%) | |
|---|---|---|---|---|
| | | | Histamine | SRS-A |
| 118 | 23 | 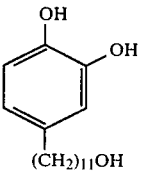 (CH₂)₁₁OH | 10.7 | 69.6 |
| 117 | 25A | 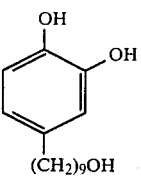 (CH₂)₉OH | −8.3 | 43.9 |
| 77 | 29 | 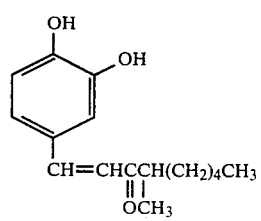 CH=CHCCH(CH₂)₄CH₃<br>‖ ‖<br>OCH₃ | −32.4 | 38.2 |

[1]The results represent the mean of 3 rats.

As shown in Table 1, the compounds of this invention more effectively inhibited the antigen-induced SRS-A release than histamine release, whereas DSCG inhibited the histamine release in a relatively selective manner.

These results suggest that there is a difference of the actions between the compounds of this invention and DSCG.

(B) Assay of 5-lipoxygenase and cyclooygenase

The method was based on that of Koshihara et al[1]. In the case of assay of 5-lipoxygenase activity, an enzyme fraction from mastocytoma P-815 cells ($10^7$ cells/ml) was incubated with 0.2 μCi [1-$^{14}$C]-arachidonic acid (56.9 Ci/mol), 0.8 mM $CaCl_2$, $2\times10^{-5}$M indoemthacin and various concentrations of test drugs at 37° C. for 5 min. In the case of assay of cyclooxygenase activity, $CaCl_2$ and indomethacin were omitted from the above incubation mixture and incubation was performed at 37° C. for 7 min. Both reactions were terminated by adjusting the pH of the mixture to 3.0 with HCl. After extraction of the products with 8 volume ethyl acetate, each extract was concentrated and applied to TLC plate. For the separation of HETEs and prostaglandins, thin-layer chromatography was carried out using the solvent system: petroleum ether/diethyl ether/acetic acid (50:50:1) and ethyl acetate/2,2,4-trimethylpentane/acetic acid/water (11:5:2:10, upper phase), respectively. Radioactive spots were detected by autoradiography and scraped off and counted using a liquid scintillation spectrometer. The activities of 5-lipoxygenase and cyclooxygenase were expressed as the sum of radioactivities due to 5-HETE and 5,12-diHETE and due to $PGD_2$, $PGE_2$ and $PGF_{2\alpha}$, respectively. The IC 50 values were calculated by Probit method.

(1) Koshihara et al. (1982) FEBS Letters 143, 13–16.

TABLE 2

| ALT No. | Example | Drug Formula | IC 50 (μM) | |
|---|---|---|---|---|
| | | | 5-Lipoxygenase | Cyclooxygenase |
| 18 | 1 |  CH₂CH₂CHCH(CH₂)₃CH₃<br>    \| \|<br>    OH CH₃ | 0.30 | Enhanced |
| 70 | 9 | 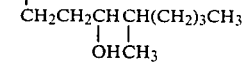 CH₂CH₂CH(CH₂)₇CH₃<br>    \|<br>    OH | 0.10 | >10 |
| 103 | 20 | 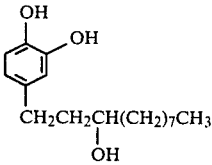 (CH₂)₇CCH₃<br>‖<br>O | 0.23 | >10 |
| 118 | 23 | 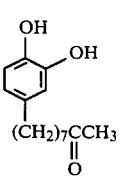 (CH₂)₁₁OH | 0.054 | >10 |

The compounds of this invention dose-dependently inhibited the formation of 5-lipoxygenase products in doses between 0.1 to 10 μM; their IC 50 values were shown in Table 2. On the contrary, at 10 μM they showed weak inhibition or enhancement of the formation of cyclooxygenase products.

These results indicate that the compounds of this invention specifically inhibit 5-lipoxygenase.

The compounds of this invention shown by general formula (I) can be stably administered orally or parenterally by themselves or as medicament compositions [e.g., tablets, capsules (including soft capsules, microcapsules, etc.,), powders, granules, pills, ointments, syrups, injections, inhalators, plasters, etc.,] mixed with known pharmaceutically allowable carriers, excepients, etc. The doses thereof depend upon the subject to be administered, the manner of administration, the condition of disease, etc., but are ordinarily 0.1 to 500 mg per day per adult and it is proper to administer them orally or parenterally two or three times per day.

The compounds of this invention shown by general formula (I) can be prepared by the methods shown in the following reaction formulae:

(wherein m' represents 0 or an integer of 1 to 13), a group represented by the formula

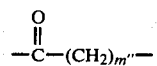

(wherein m" represents an integer of 1 to 14), or a group represented by the general formula

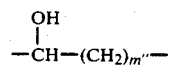

(wherein m" has the same significance as above); said $-(CH_2)_{m'}-$ and $-(CH_2)_{m''}-$ may have branch; Y' repersents a carbonyl group or a group shown by

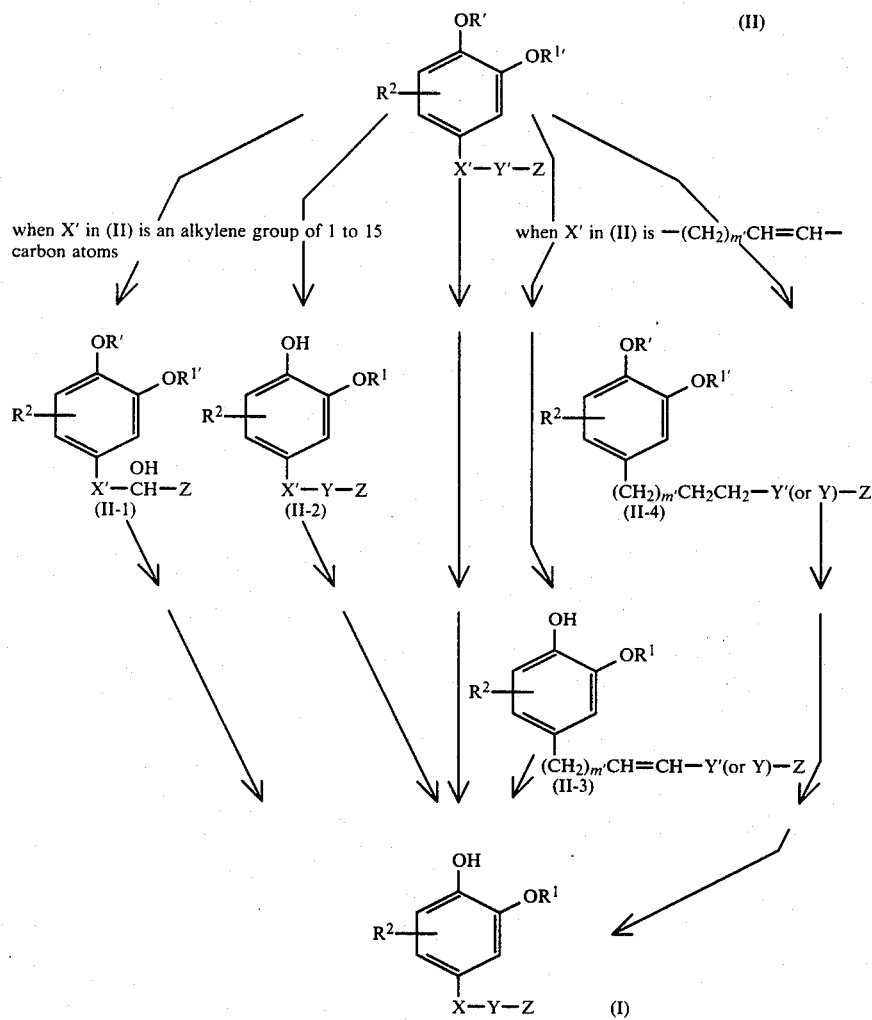

wherein $R^1$, $R^2$, X, Y, and Z have the same significance as defined above; R' represents a protective group for the hydroxy group capable of being easily removed; $R^{1'}$ represents a protective group for the hydroxy group capable of being easily removed or a lower alkyl group; X' represents a straight chain or branched alkylene group having 1 to 15 carbon atoms, an alkenylene group represented by the formula $-(CH_2)_{m'}CH=CH-$

($R^{3'}$ and $R^4$, which may be the same or different, each represents a hydrogen atom or a lower alkyl group; said $R^{3'}$ may mean a protective group for a hydroxy group); the sum of said X' and Z being at least 3.

In the above-described methods, a 1-(3-hydroxy(or 3-lower alkoxy)-4-hydroxyphenyl)alkane of general formula (I) is produced by reducing or hydrolyzing the corresponding 1-(3,4-disubstituted pheyl)alkane or 1-(3,4-disubstituted phenyl)alkene. The reduction includes (a) the removal of the protective group for the hydroxy group, (b) the the reduction of a carbonyl group $$(-\overset{\overset{O}{\|}}{C}-)$$

shown by Y' into a hydroxymethylene group $$(-\overset{\overset{OH}{|}}{CH}-),$$

and (c) the saturation of an unsaturated bond (alkenylene group→alkylene group).

The reduction may be performed in an optional order. Also, by properly selecting the conditions, the reduction may be a partial reduction.

The removal of the protection group for hydroxy group of the foregoing reduction (a) differs according to the kind of the protective group. In the production method of the compounds of this invention, a benzyl group, a p-methoxybenzyl group, a benzyloxycarbonyl group, a methoxymethyl group, an acetyl group, a benzoyl group, etc., are employed as a protective group and the removal of the protective group is usually performed by a catalytic reduction using palladium-carbon as a catalyst, the reduction by metallic sodium in liquid ammonia, an acid hydrolysis or an alkali hydrolysis.

The conversion of a carbonyl group into a corresponding hydroxymethylene group of reduction (b) is performed by a chemical reduction using aluminum lithium hydride (LiAlH$_4$), sodium boron hydride (NaBH$_4$), etc., or a catalytic reduction using palladium-carbon, etc.

Also, the reduction of an alkenylene group (—(CH$_2$)$_{m'}$CH=CH—) into an alkylene group (—(CH$_2$)$_{m'}$CH$_2$CH$_2$—) of the reduction (c) is performed by a catalytic reducting using palladium-carbon, Raneynickel catalyst, platinum black, etc.

For the production methods of the compounds of this invention shown by general formula (I), there are further a halogenation of a benzene ring, a lower alkoxylation of a hydroxy group, etc. These reactions are performed by ordinary procedures.

Then, the following examples are intended to illustrate the compounds of this invention shown by formula (I) and the production methods of the compounds but are not limiting in any way.

In addition, since the raw materials used in the following examples include novel compounds, the production methods of these compounds are explained by the following reference examples.

REFERENCE EXAMPLE 1 (a)

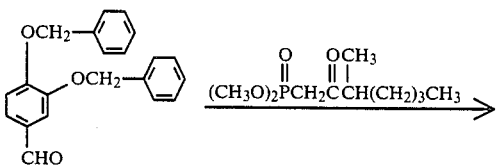

-continued

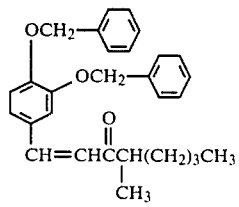

While stirring a mixture of 400 mg of oily sodium hydride (60%) and 50 ml of 1,2-dimethoxyethane, a mixture of 2.36 g of dimethyl/(3-methyl-2-oxo)heptyl phosphonate and 5 ml of dimethoxyethane was added dropwise to the mixture at 20° to 25° C. Then, after stirring the resultant mixture for 2 hours at room temperature, the reaction mixture was cooled to 5° to 7° C. and a mixture of 2.3 g of 3,4-dibenzyloxybenzaldehyde and 5 ml of dimethoxyethane was added dropwise to the reaction mixture.

After stirring the reaction mixture for 2 hours at room temperature, 300 ml of water was added to the reaction mixture and the product was extracted with 50 ml of toluene-n-hexane (1:1). The extract was washed with water, dried over anhydrous magnesium sulfate, and concentrated under reduced pressure to provide a sticky residue. The residue was applied to silica gel (70 ml) column chromatography and eluted with a mixture of n-hexane and ether (4:1) to provide 1.2 g of 1-(3,4-dibenzyloxyphenyl)-4-methyl-1-octen-3-one.

Melting point 62°-64° C.

REFERENCE EXAMPLE 1 (b)

(Raw material in Example 1)

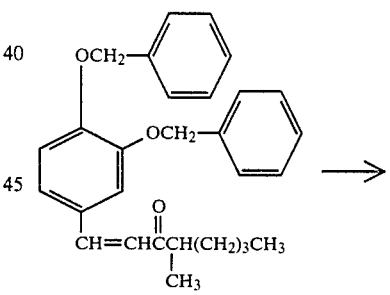

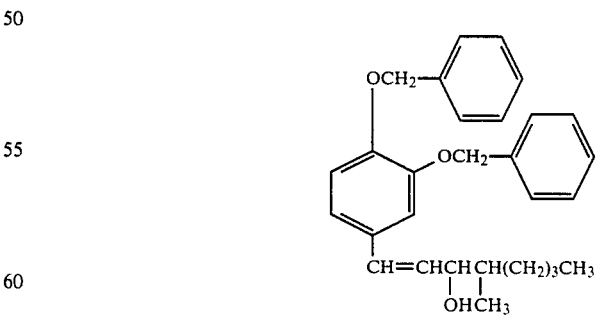

To a mixture obtained by adding 0.1 g of lithium aluminum hydride to 20 ml of ether was added 0.55 g of 1-(3,4-dibenzyloxyphenyl)-1-octen-3-one under ice-cooling and the mixture was stirred for one hour at room temperature. To the reaction mixture was gradually added 10 ml of an aqueous 10% hydrochloric acid solution and the ether layer was collected, washed with water, and concentrated under reduced pressure to provide a solid product. By washing the product with a mixture of ether and n-hexane (1:3), 0.4 g of 1-(3,4-dibenzyloxyphenyl)-4-methyl-1-octen-3-ol was obtained.

Melting point 77°–78° C.

Then, by following the same procedures as in Reference Example 1 (a) and (b), the following compounds of Reference Example 2 (a) and (b) were obtained and by following the same procedure as in Reference Example 1 (a), the following compounds of Reference Examples 3 to 7 were obtained.

REFERENCE EXAMPLE 2 (a)

(Raw material in Example 3)

1-(3,4-Dibenzyloxyphenyl)-1-nonen-3-one. Melting point 78°–80° C.

| Elemental analysis for $C_{29}H_{32}O_3$: | | |
|---|---|---|
| | C | H |
| Calculated: | 81.27% | 7.53% |
| Found: | 81.21% | 7.65% |

REFERENCE EXAMPLE 2 (b)

(Raw material in Example 2)

(Using the compound obtained in the above step (a))

1-(3,4-Dibenzyloxyphenyl)-1-nonen-3-ol. Melting point 90°–92° C.

REFERENCE EXAMPLE 3

(Raw material in Example 4)

1-(3,4-Dibenzyloxyphenyl)-1-pentadecen-3-one.
Melting point 81°–82° C.

| Elemental analysis for $C_{35}H_{44}O_3$: | | |
|---|---|---|
| | C | H |
| Calculated: | 81.99% | 8.65% |
| Found: | 81.78% | 8.81% |

REFERENCE EXAMPLE 4

(Raw material in Example 5)

1-(3,4-Dibenzyloxyphenyl)-4-ethyl-1-octen-3-one.
Oily product.

Nuclear magnetic resonance spectra (in $CDCl_3$, TMS internal standard, ppm.)

0.86(6H), 1.1–1.9(8H), 2.65(1H), 5.15(4H), 6.4–7.6(15H).

REFERENCE EXAMPLE 5

(Raw material in Example 6)

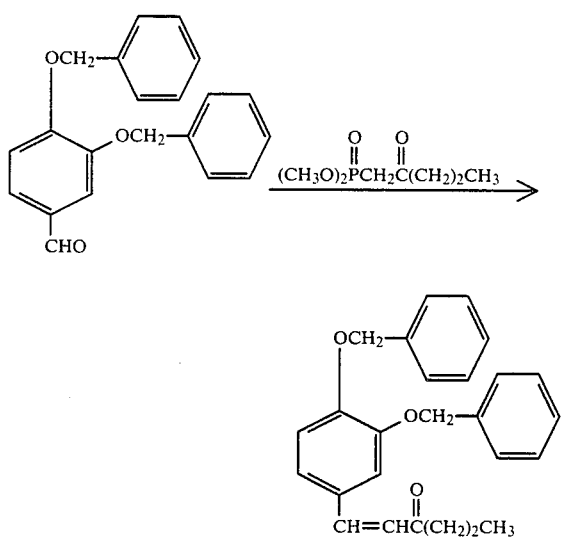

1-(3,4-Dibenzyloxyphenyl)-1-hexen-3-one.
Melting point 82°–84° C.

| Elemental analysis for $C_{26}H_{26}O_3$: | | |
|---|---|---|
| | C | H |
| Calculated: | 80.80% | 6.78% |
| Found: | 80.80% | 6.81% |

REFERENCE EXAMPLE 6

(Raw material in Example 7)

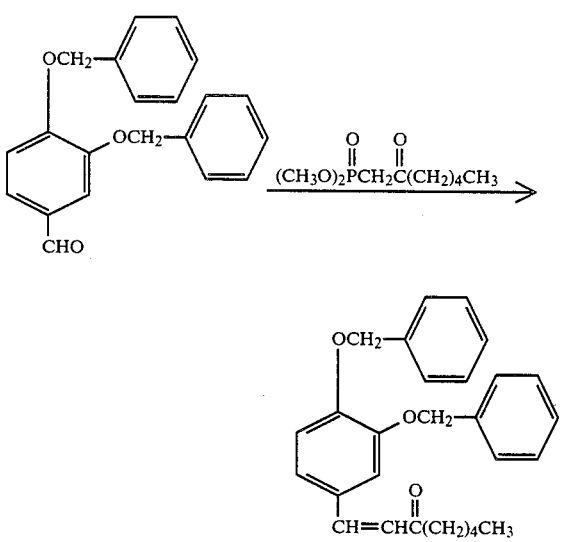

1-(3,4-Dibenzyloxyphenyl)-1-octen-3-one.
Melting point 71°–73° C.

| Elemental analysis for $C_{28}H_{30}O_3$: | | |
|---|---|---|
| | C | H |
| Calculated: | 81.13% | 7.29% |
| Found: | 80.91% | 7.47% |

REFERENCE EXAMPLE 7

(Raw material in Example 8)

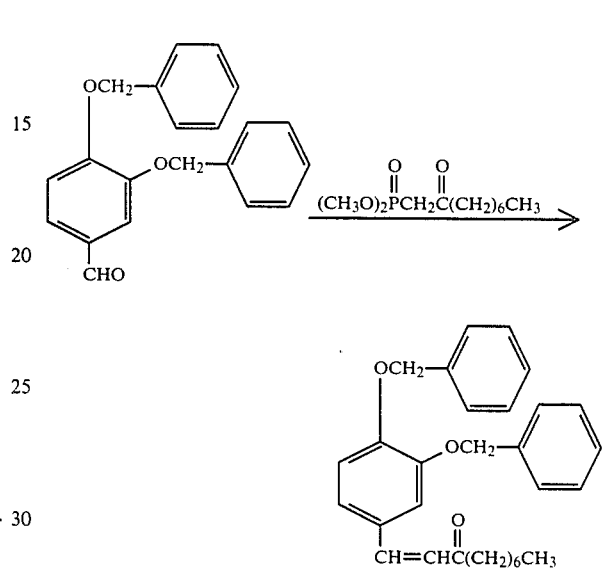

1-(3,4-Dibenzyloxyphenyl)-1-decen-3-one.
Melting point 73°–75° C.

| Elemental analysis for $C_{30}H_{34}O_3$: | | |
|---|---|---|
| | C | H |
| Calculated: | 81.41% | 7.74% |
| Found: | 81.26% | 7.97% |

In addition, the properties and production methods of dimethyl 2-oxoalkylphosphonates used in the above reference examples are shown below.

Method A

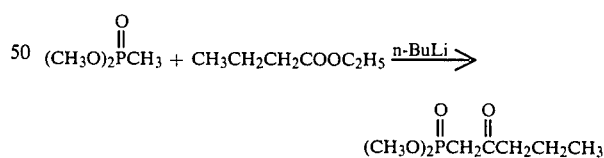

In 65 ml of anhydrous tetrahydrofuran was dissolved 12.75 g of dimethyl methylphosphonate and the solution was cooled below −70° C. Then, while stirring the solution under nitrogen stream, 67 ml of a hexane solution (10 v/w%) of n-butyl lithium (n-BuLi) cooled below −70° C. was added dropwise to the solution over a 30 minute period and the mixture was stirred for 15 minutes at the same temperature. Then, a solution of 5.8 g of ethyl n-butyrate in 15 ml of anhydrous tetrahydrofuran cooled below −70° C. was added dropwise to the mixture over a 15 minute period and the resultant mixture was stirred for 1.5 hours below −70° C. and then for 2 hours at room temperature.

The reaction mixture thus obtained was ice-cooled, mixed with 10 ml of glacial acetic acid, and the solvent was distilled off from the mixture under reduced pressure. To the residue was added 50 ml of water and the product was extracted three times each time with 50 ml of ethyl ether. The extracts were combined with each other and washed twice each time with 20 ml of a saturated aqueous sodium chloride solution. After drying the extract with anhydrous magnesium sulfate, the solvent was distilled off under reduced pressure and the residue was vacuum-distilled to provide 9.7 g of dimethyl 2-oxopentylphosphonate.

Boiling point 95°–97° C./0.9 mm Hg.

By following the procedure as in Method A, the phosphonate compounds having the following formulae were prepared.

|  | Boiling Point |
|---|---|
| $(CH_3O)_2\overset{O}{\overset{\|}{P}}CH_2\overset{O}{\overset{\|}{C}}(CH_2)_4CH_3$ | 113–115° C./0.8 mm Hg |
| $(CH_3O)_2\overset{O}{\overset{\|}{P}}CH_2\overset{O}{\overset{\|}{C}}(CH_2)_6CH_3$ | 129–132° C./0.9 mm Hg |
| $(CH_3O)_2\overset{O}{\overset{\|}{P}}CH_2\overset{OCH_2CH_3}{\overset{\|}{C}}H(CH_2)_3CH_3$ | 126–128° C./0.85 mm Hg |
| $(CH_3O)_2\overset{O}{\overset{\|}{P}}CH_2\overset{OCH_3}{\overset{\|}{C}}H(CH_2)_3CH_3$ | 104–108° C./0.25 mm Hg |
| $(CH_3O)_2\overset{O}{\overset{\|}{P}}CH_2\overset{O}{\overset{\|}{C}}(CH_2)_5CH_3$ | 120–123° C./0.4 mm Hg |

Method B:

$(CH_3O)_2\overset{O}{\overset{\|}{P}}CH_2\overset{O}{\overset{\|}{C}}(CH_2)_{11}CH_3$ A mixture of 2.5 g of dimethyl methylphosphonate and 15 ml of anhydrous tetrahydrofuran was cooled below −70° C. and 13.5 ml of a hexane solution (10 v/w%) of n-butyl lithium cooled below −70° C. was added dropwise to the mixture with stirring under nitrogen stream over a 30 minute period followed by stirring for 15 minutes at the same temperature. Then, a mixture of 2.4 g of ethyl tridecanoate and 5 ml of anhydrous tetrahydrofuran was added dropwise to the mixture over a 10 minute period and the resultant mixture was stirred for 1 hour at a temperature below −70° C. and then for 2 hours at room temperature.

The reaction mixture thus obtained was ice-cooled, mixed with 2 ml of glacial acetic acid, the mixture was concentrated under reduced pressure, and then extracted three times each time with 10 ml of ethyl ether. The extracts were combined, washed with a saturated aqueous sodium chloride solution, dried over anhydrous magnesium sulfate, and concentrated under reduced pressure to provide an oily product. The oily product was applied to silica gel (40 ml) column chromatography and eluted with ethyl ether to provide 2.5 g of dimethyl 2-oxotetradecanoylphosphonate.

Boiling point 37°–38° C.

REFERENCE EXAMPLE 8

(Raw material in Example 13)

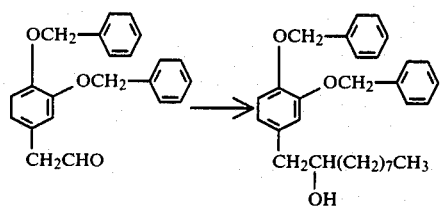

After gradually adding 0.5 g of 3,4-dibenzyloxyphenylacetaldehyde to 10 mg of an ether solution of n-octylmagnesium bromide obtained from 0.12 g of magnesium and 0.97 g of n-octyl bromide, the mixture was stirred for 30 minutes at room temperature. To the reaction mixture thus obtained was added 10 ml of an aqueous 5% hydrochloric acid solution and after stirring the mixture, the ether layer was collected. The ether solution was washed with water, dried over anhydrous magnesium sulfate, and concentrated under reduced pressure to provide 0.5 g of 1-(3,4-dibenzyloxyphenyl)-2-decanol.

Melting point 55°–57° C. (n-hexane).

| Elemental analysis for $C_{30}H_{38}O_3$: | | |
|---|---|---|
|  | C | H |
| Calculated: | 80.54% | 8.78% |
| Found: | 80.68% | 8.58% |

By following the procedure as in Reference Example 8, the following compounds (Reference Examples 9 to 11) were prepared. The names of these compounds are shown below together with the melting points and/or nuclear magnetic resonance spectra (in CDCl₃, TMS internal standard, ppm).

REFERENCE EXAMPLE 9

(Raw material in Example 16)

1-(3,4-Dibenzyloxyphenyl)-2-nonanol.
0.7–1.6(15H), 2.57(2H), 3.63(1H), 5.08(4H), 6.5–7.5(13H).

REFERENCE EXAMPLE 10

(Raw material in Example 17)

1-(3,4-Dibenzyloxyphenyl)-2-undecanol.
Melting point 55°–57° C.
0.7–1.6(19H), 2.57(2H), 3.59(1H), 5.07(4H), 6.5–7.5(13H).

| Elemental analysis for $C_{31}H_{40}O_3$: | | |
|---|---|---|
|  | C | H |
| Calculated: | 80.83% | 8.75% |
| Found: | 80.83% | 8.89% |

REFERENCE EXAMPLE 11

(Raw material in Example 18)

2-(3,4-Dibenzyloxyphenyl)-1-cyclohexyl-1-ethanol.
Melting point 73°–75° C.

| Elemental analysis for $C_{28}H_{32}O_3$: | | |
|---|---|---|
| | C | H |
| Calculated: | 80.73% | 7.74% |
| Found: | 80.65% | 7.80% |

REFERENCE EXAMPLE 12

(Raw material in Example 14)

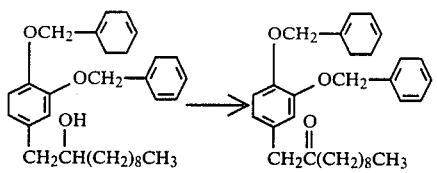

To a mixture of 15 ml of methylene chloride and 1.2 ml of pyridine was gradually added 2 g of chromic anhydride under cooling to 0° C. to −5° C. and after stirring the mixture for 10 minutes at 0° to −3° C., a solution of 0.9 g of 3,4-dibenzyloxyphenyl-2-undecanol in 3 ml of methylene chloride was added to the mixture. After further stirring the mixture for 20 minutes at 0° to 10° C., the supernatent methylene chloride solution was concentrated under reduced pressure. The residue was applied to silica gel column chromatography and eluted with toluene to provide 0.8 g of 1-(3,4-dibenzyloxyphenyl)-2-undecanone.

Melting point 68° C.

| Elemental analysis for $C_{31}H_{38}O_3$: | | |
|---|---|---|
| | C | H |
| Calculated: | 81.18% | 8.35% |
| Found: | 81.13% | 8.28% |

REFERENCE EXAMPLE 13

(Raw material in Example 15)

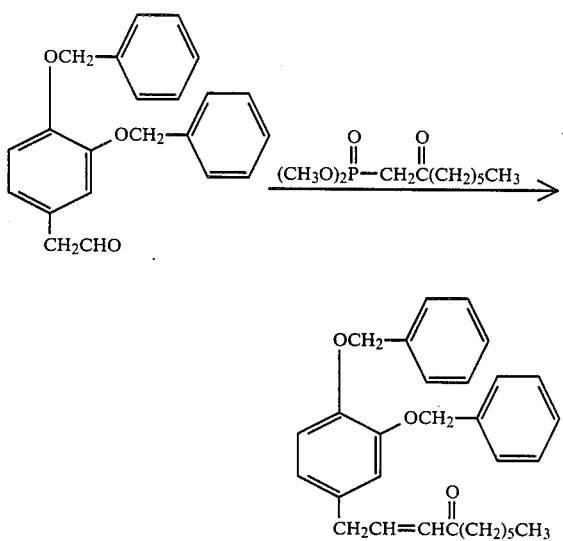

To a solution obtained by adding 200 mg of oily sodium hydride (60%) to a mixture of 25 ml of 1,2-dimethoxyethane and 10 ml of dimethyl sulfoxide was added dropwise a mixture of 1.2 g of dimethyl 2-oxooctylphosphonate and 3 ml of dimethoxyethane at 20° to 25° C. Thereafter, the mixture was stirred for 2 hours at room temperature and after adding thereto small pieces of dry ice, the mixture was further stirred for 5 minutes. To the reaction mixture was added 200 ml of water and the product was extracted with toluene. The extract was washed with water, dried over anhydrous magnesium sulfate, and concentrated under reduced pressure. The residue was applied to silica gel column chromatography and eluted with a mixture of toluene and ethyl acetate (10:1) to provide 0.5 g of 1-(3,4-dibenzyloxyphenyl)-2-decen-4-one as an oily product.

Nuclear magnetic resonance spectra (in CDCl$_3$, TMS internal standard, ppm) 0.7–1.8(11H), 2.42(2H), 3.24(2H), 5.09(4H), 6.0–7.7(15H).

REFERENCE EXAMPLE 14

(Raw material in Example 19)

By following the procedure as in Reference Example 13, 1-(3,4-dibenzyloxyphenyl)-3-decen-5-one was obtained from 1-(3,4-dibenzyloxyphenyl)propionaldehyde and dimethyl 2-oxohexylphosphonate.

Melting point 38°–39° C.

| Elemental analysis for $C_{30}H_{34}O_3$: | | |
|---|---|---|
| | C | H |
| Calculated: | 81.41% | 7.74% |
| Found: | 81.48% | 7.66% |

REFERENCE EXAMPLE 15

(Raw material in Example 20)

(a)

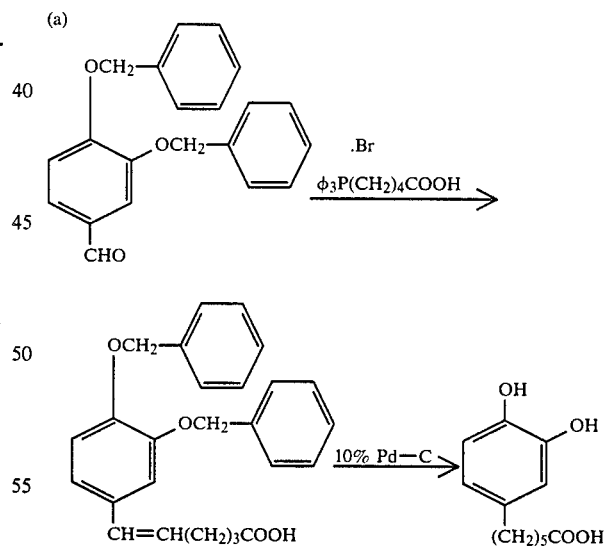

A mixture of 2 g of oily sodium hydride (60%) and 90 ml of dimethyl sulfoxide was stirred for 1 hour at 55°–60° C. and then allowed to cool to room temperature. To the mixture was added dropwise a mixture of 11 g of (4-carboxybutyl)triphenylphosphonium bromide and 25 ml of dimethyl sulfoxide at room temperature. Thereafter, the mixture was stirred for 30 minutes at room temperature and then to the reaction mixture was added dropwise a mixture of 8 g of 3,4-dibenzyloxybenzaldehyde and 30 ml of dimethyl sulfoxide. After further stirring the mixture for one hour at room temperature, 5 g of dry ice was added to the reaction mixture and after further adding thereto 250 ml of water and 50 ml of an aqueous 10% hydrochloric acid solution, the product was extracted with 300 ml of ether. The extract was washed with water, dried over anhydrous magnesium sulfate, and concentrated under reduced pressure to provide a sticky product. The product was applied to silica gel (150 ml) column chromatography and eluted with a mixture of n-hexane and ether (1:1) to provide 8.5 g of 6-(3,4-dibenzyloxyphenyl)-5-hexenoic acid. The product was dissolved in 30 ml of ethanol and catalytically reduced using 1 g of 10% palladium-carbon as a catalyst until the absorption of hydrogen stopped. Then, the catalyst was removed by filtration and the filtrate was concentrated under reduced pressure to provide 3.8 g of 6-(3,4-dihydroxyphenyl)hexanoic acid. Melting point 109° C.

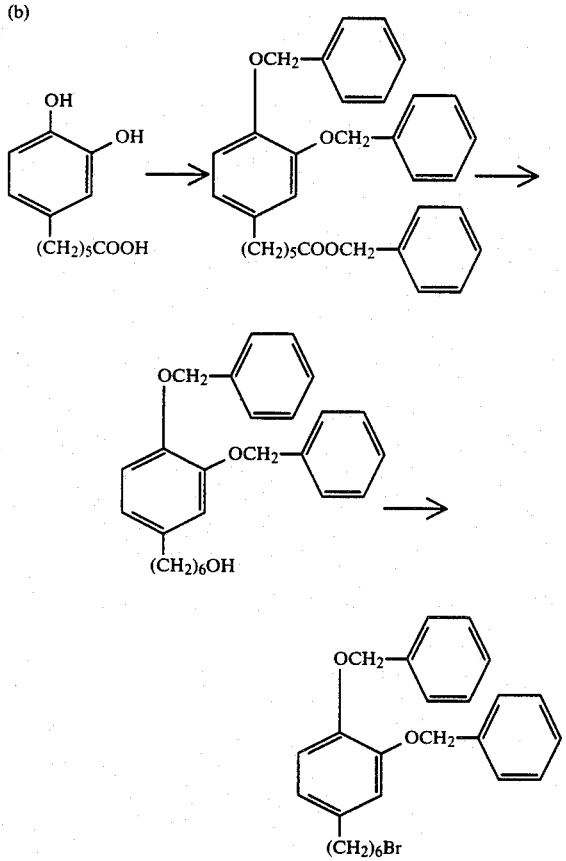

A mixture of 3.8 g of 6-(3,4-dihydroxyphenyl)hexanoic acid, 8.6 g of benzyl chloride, 9.4 g of potassium carbonate, 0.1 g of potassium iodide, 0.1 g of tetra-n-butylammonium bromide, and 50 ml of N,N-dimethylformamide was stirred overnight at room temperature. After the reaction was over, 200 ml of water was added to the reaction mixture and the product was extracted three times each time with 100 ml of ether. The extracts were combined with each other, washed with water, dried over anhydrous magnesium sulfate, and concentrated under reduced pressure to provide a sticky product. The product was applied to silica gel (150 ml) column chromatography and eluted with a mixture of toluene and ethyl acetate (19:1) to provide 3.4 g of benzyl 6-(3,4-dibenzyloxyphenyl)hexanate.

The product thus obtained was dissolved in 20 ml of ether and the solution was added dropwise to a mixture of 0.5 g of lithium aluminum hydride and 50 ml of ether under ice-cooling. Thereafter, the mixture was stirred for one hour at room temperature and 30 ml of an aqueous 10% hydrochloric acid solution was added to the reaction mixture under ice-cooling. The organic layer thus formed was collected, washed with water, dried over anhydrous magnesium sulfate, and concentrated under reduced pressure to provide a sticky product. The product was applied to silica gel (100 ml) column chromatography and eluted with a mixture of toluene and ethyl acetate (4:1) to provide 1.95 g of 6-(3,4-dibenzyloxyphenyl)hexanol.

The product was dissolved in 10 ml of methylene chloride and the solution was added dropwise at room temperature to a methylene chloride solution (containing 0.45 g of pyridine) of triphenylphosphinedibromide prepared from 1.57 g of triphenylphosphine and 0.88 g of bromine. Thereafter, the mixture was stirred overnight at room temperature and the reaction mixture thus obtained was washed with diluted hydrochloric acid, washed with water, dried over anhydrous magnesium sulfate, and concentrated under reduced pressure. The residue was applied to silica gel (50 ml) column chromatography and eluted with a mixture of n-hexane and toluene (2:1) to provide 1.08 g of 6-(3,4-dibenzyloxyphenyl)hexyl bromide as an oil.

Nuclear magnetic resonance spectra (in CDCl$_3$, TMS internal standard, ppm); 1.0–2.0(8H), 2.50(2H), 3.38(2H), 5.13(2H), 5.16(2H), 6.6–6.92(3H), 7.10–7.60(10H).

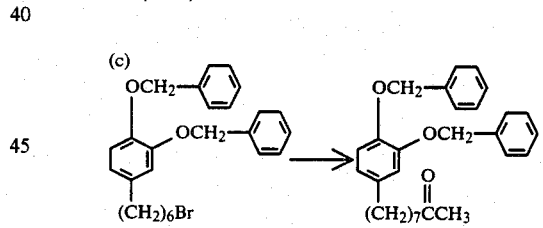

A mixture of 0.5 g of 6-(3,4-dibenzyloxyphenyl)hexyl bromide, 0.12 g of acetylacetone, 0.15 g of potassium carbonate, 0.02 g of sodium iodide, and 5 ml of ethanol was refluxed for 20 hours. To the reaction mixture was added 15 ml of water and the product was extracted with 20 ml of ether. The extract was washed with water, dried over anhydrous magnesium sulfate, and concentrated under reduced pressure to provide a sticky product. The product was applied to silica gel (45 ml) column chromatography and eluted with a mixture of toluene and ethyl acetate (30:1) to provide 33 mg of 9-(3,4-dibenzyloxyphenyl)-2-nonanone as an oil.

Nuclear magnetic resonance spectra (in CDCl$_3$, TMS internal standard, ppm): 1.0–2.0(10H), 2.10(3H), 2.20–2.70(4H), 3.08(2H), 3,10(2H), 6.50–7.0(3H), 7.20–7.60(10H).

REFERENCE EXAMPLE 16

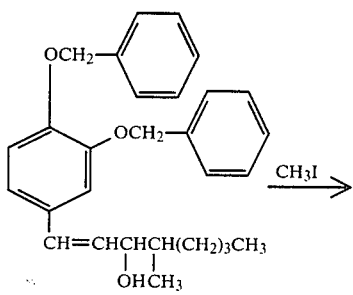

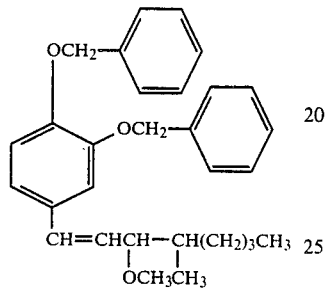

To a mixture of 130 mg of oily sodium hydride (60%) and 15 ml of N,N-dimethylformamide were added dropwise, in succession, a solution of 1.27 g of 1-(3,4-dibenzyloxyphenyl)-4-methyl-1-octen-3-ol obtained in Reference Example 1 in 5 ml of N,N-dimethylformamide and 500 mg of methyl iodide with stirring under ice-cooling. After stirring the mixture overnight at room temperature, 150 ml of water was added to the reaction mixture and the product was extracted with 30 ml of ethyl acetate. The extract was washed with water, dried over anhydrous magnesium sulfate, and concentrated under reduced pressure to provide a sticky product. The product was applied to silica gel (40 g) column chromatography and eluted with a mixture of n-hexane and ether (4:1) to provide 970 mg of 1-(3,4-dibenzyloxyphenyl)-3-methoxy-4-methyl-1-octene. Melting point 36°–38° C.

REFERENCE EXAMPLE 17

(Raw material in Example 23)

(a)

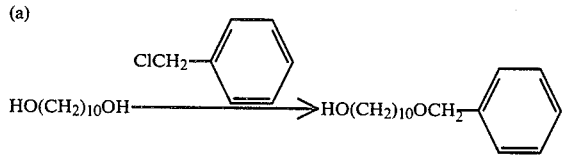

In 20 ml of xylene was dissolved 35 g of decanediol by heating and after adding thereto 1.65 g of metallic sodium at 130° C., the mixture was heated for one hour at 125° to 130° C. To the reaction mixture was added dropwise 9.5 g of benzyl chloride at 120°–130° C. and the mixture was further heated for one hour at 130° C. The reaction mixture was cooled to 110° C. and after adding thereto 50 ml of toluene, the mixture was filtered while the mixture was in a hot state. The filtrate was ice-cooled to precipitate crystals, which were collected by filtration to recover 24 g of decanediol used as the raw material. On the other hand, the filtrate was concentrated under reduced pressure to provide an oily product. The product was applied to silica gel column chromatography and eluted with a mixture of toluene and ethyl acetate (8:2) to provide 13 g of oily 10-benzyloxy-1-decanol.

Nuclear magnetic resonance spectra (in CDCl$_3$, TMS, ppm): 1.1–2.0(16H, (CH$_2$)$_8$), 3.43(2H, t, —CH$_2$O—), 3.59(2H, t, —C$\underline{H}_2$—OH), 4.47(2H, s,

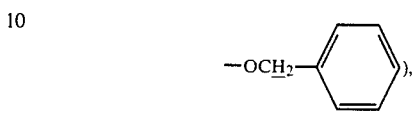

7.28(5H, H of benzene ring).

(b)

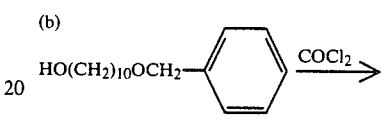

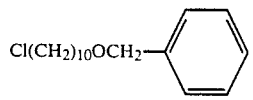

A mixture of 7 g of 10-benzyloxy-1-decanol, 8 ml of thionyl chloride, and 0.2 ml of dimethylformamide was heated to 50° to 60° C. for one hour. After the reaction was over, the reaction mixture was concentrated under reduced pressure, the residue was dissolved in 50 ml of n-hexane, and after washing the solution with water, the solution was dried over anhydrous magnesium sulfate. Then, the solvent was distilled off and the residue was applied to silica gel column chromatography and eluted with toluene to provide 6.7 g of oily 10-benzyloxy-1-chlorodecane. Boiling point 135°–140° C. (0.6–0.9 mm Hg).

Nuclear magnetic resonance spectra (in CDCl$_3$, TMS, ppm): 1.1–2.0(16H, (CH$_2$)$_8$), 3.43(2H, t, —CH$_2$—O—), 3.49(2H, t, —CH$_2$Cl), 4.47(2H, s, —OCH$_2$—), 7.28(5H, H of benzene ring).

(c)

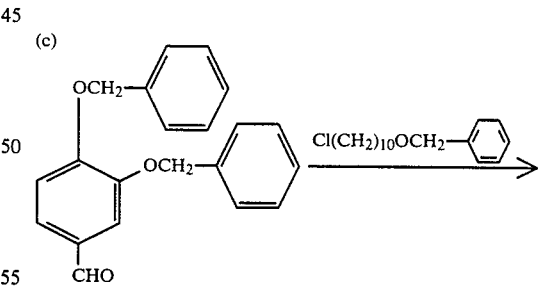

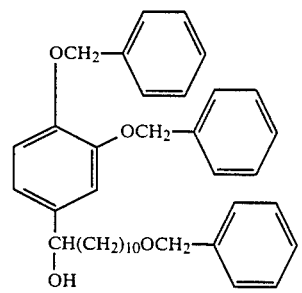

To a mixture of 1 ml of anhydrous ether and 0.6 g of metallic magnesium were added 0.1 ml of ethyl iodide and a piece of iodine crystal followed by heating to initiate the reaction and then a mixture of 6.7 g of 10-benzyloxy-1-chlorodecane and 10 ml of anhydrous ether was added dropwise to the aforesaid mixture. After the reaction was over, the reaction mixture was refluxed for 2 hours. After cooling, the reaction mixture was added dropwise to a solution of 6 g of 3,4-dibenzyloxybenzaldehyde dissolved in 30 ml of tetrahydrofuran at 0° to 5° C. Thereafter, the mixture was stirred for 30 minutes at room temperature and after adding 300 ml of an aqueous 1% hydrochloric acid solution to the reaction mixture, the product was extracted with 100 ml of toluene. The extract was washed with water, dried over anhydrous magnesium sulfate, and then the solvent was distilled off under reduced pressure. The residue was dissolved in 30 ml of ethanol, the solution was allowed to stand overnight under cooling to 0° to 5° C., and the crystals thus precipitated were collected by filtration. By drying the crystals, 5 g of 11-benzyloxy-1-(3,4-dibenzyloxyphenyl)-1-undecanol was obtained. Melting point 50°-52° C.

| Elemental analysis for $C_{38}H_{46}O_4$: | | |
|---|---|---|
| | C | H |
| Calculated: | 80.53% | 8.18% |
| Found: | 80.55% | 7.94% |

REFERENCE EXAMPLE 18

(Raw material in Example 24)

(a) To a mixture of 2.16 g of benzyl alcohol and 30 ml of dimethylformamide was added 1.2 g of oily sodium hydride (60%). After stirring the mixture for 30 minutes at 20° to 25° C., 10 g of 1,12-dibromododecane was added to the mixture in one portion followed by stirring for 2 hours at 25° to 30° C. After the reaction was over, 300 ml of water was added to the reaction mixture and the product was extracted with n-hexane. The extract was washed with water, dried over anhydrous magnesium sulfate, and then, the solvent was distilled off. The oily residue was applied to silica gel column chromatography and eluted with a mixture of n-hexane and ether (9:1) to provide 3.8 g of 12-benzyloxy-1-bromododecane as an oily product.

Nuclear magnetic resonance spectra (in CDCl₃, TMS, ppm): 1.1–2.0(20H, —(CH₂)₁₀—), 3.38(2H, t, —CH₂—Br), 3,44(2H, t, —CH₂—O—), 4.47(2H, s,

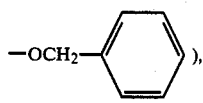), 7.28(5H, H of benzene ring)

(b) By following the procedure as in Reference Example 17-(c) using the compound in the above step (a), the following compound was obtained.

13-Benzyloxy-1-(3,4-dibenzyloxyphenyl)-1-tridecanol. Melting point 51°-53° C.

| Elemental analysis for $C_{40}H_{50}O_4$: | | |
|---|---|---|
| | C | H |
| Calculated: | 80.77% | 8.47% |

| Elemental analysis for $C_{40}H_{50}O_4$: | | |
|---|---|---|
| | C | H |
| Found: | 81.01% | 8.74% |

REFERENCE EXAMPLE 19A (Raw material in Example 25A)

(a) By following the procedure as in Reference Example 18(a) using 1,8-dibromooctane, 8-benzyloxy-1-bromooctane was obtained as an oily product.

Nuclear magnetic resonance spectra (in CDCl₃, TMS, ppm): 1.1–2.1(12H, —(CH₂)₆—), 3.38(2H, t, —CH₂Br), 3.44(2H, t, —CH₂O—), 4.47(2H, s,

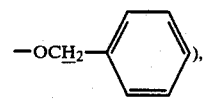

7.28(5H, H of benzene ring).

(b) By following the procedure as in Reference Example 17(c) using the compound obtained in the above step (a), 9-benzyloxy-1-(3,4-dibenzyloxyphenyl)-1-nonanol was obtained. Melting point 46°-48° C.

| Elemental analysis for $C_{36}H_{42}O_4$: | | |
|---|---|---|
| | C | H |
| Calculated: | 80.26% | 7.86% |
| Found: | 80.08% | 7.90% |

REFERENCE EXAMPLE 19B (Raw material in Example 25B)

(a) By following the procedures as in Reference Example 17(a) and (b) using nonanediol, 9-benzyloxy-1-chlorononane was obtained. Boiling point 128°-130° C. (0.6-0.7 mmHg).

(b) By following the procedure as in Reference Example 17(c) using 9-benzyloxy-1-chlorononane, 10-benzyloxy-1(3,4-dibenzyloxyphenyl)-1-decanol was obtained.

Melting point 45°-47° C.

| Elemental analysis for $C_{37}H_{44}O_4$: | | |
|---|---|---|
| | C | H |
| Calculated: | 80.40% | 8.02% |
| Found: | 80.30% | 8.02% |

REFERENCE EXAMPLE 20

(Raw material in Example 26)

By following the procedure as in Reference Example 17(c) using 4-benzyloxy-3-methoxybenzaldehyde and 10-benzyloxy-1-chlorodecane, 11-benzyloxy-1-(4-benzyloxy-3-methoxyphenyl)-1-undecanol was obtained. Melting point 43°-45° C.

| Elemental analysis for $C_{32}H_{42}O_4$: | | |
|---|---|---|
| | C | H |
| Calculated: | 78.33% | 8.63% |

| Elemental analysis for $C_{32}H_{42}O_4$: | | |
|---|---|---|
| | C | H |
| Found: | 78.24% | 8.62% |

REFERENCE EXAMPLE 21

(Raw material in Example 27)

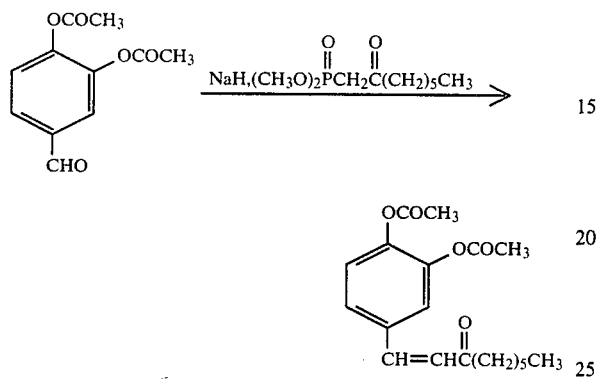

To a mixture of 400 mg of oily sodium hydride (60%) and 50 ml of 1,2-dimethoxyethane was added dropwise a mixture of 3.06 g of dimethyl 2-oxooctylphosphonate and 10 ml of dimethoxyethane with stirring under ice-cooling. After adding thereto 5 ml of dimethyl sulfoxide and stirring the mixture for one hour at room temperature, a mixture of 2.22 g of 3,4-diacetoxybenzaldehyde and 10 ml of dimethoxyethane was added dropwise to the mixture. After stirring the resultant mixture for 4 hours at room temperature, 400 ml of water was added to the reaction mixture and the product was extracted twice each time with 50 ml of ether. The extract was washed with water, dried over anhydrous magnesium sulfate, and concentrated under reduced pressure. The residue was applied to silica gel (120 g) column chromatography and eluted with a mixture of toluene and ethyl acetate (20:1) to provide 2.67 g of 1-(3,4-diacetoxyphenyl)-1-nonen-3-one.

Melting point 71°–72° C.

By following the procedure as in Reference Example 21, the compounds of following Reference Examples 22 to 24 were prepared.

REFERENCE EXAMPLE 22

(Raw material in Example 28)

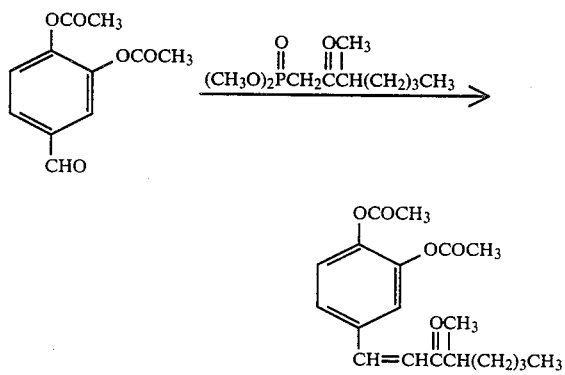

1-(3,4-Diacetoxyphenyl)-4-methyl-1-octen-3-one.
Oily product.

Nuclear magnetic resonance spectra (In CDCl₃, TMS internal standard, ppm): 0.89(3H), 1.05–1.9(9H), 2.30(6H), 2,75(1H), 6.6–7.7(5H).

REFERENCE EXAMPLE 23

(Raw material in Example 29)

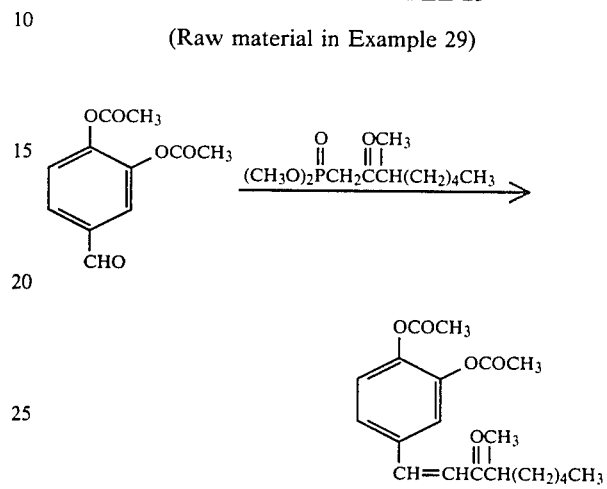

1-(3,4-Diacetoxyphenyl)-4-methyl-1-nonen-3-one.
Oily product.

Nuclear magnetic resonance spectra (in CDCl₃, TMS internal standard, ppm): 0.88(3H), 1.05–1.9(11H), 2.30(6H), 2.77(1H), 6.66–7.7(5H).

REFERENCE EXAMPLE 24

(Raw material in Example 30)

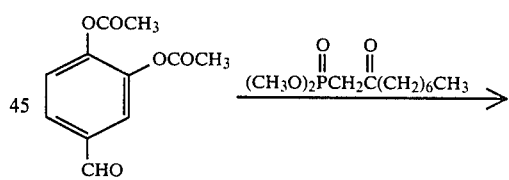

1-(3,4-Diacetoxyphenyl)-1-decen-3-one.
Melting point 66°–67° C.

| Elemental analysis for $C_{20}H_{26}O_5$: | | |
|---|---|---|
| | C | H |
| Calculated: | 69.34% | 7.56% |
| Found: | 69.33% | 7.72% |

REFERENCE EXAMPLE 25

(Raw material in Example 31)

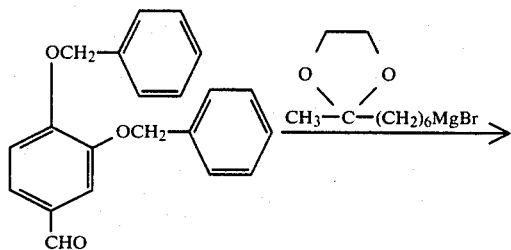

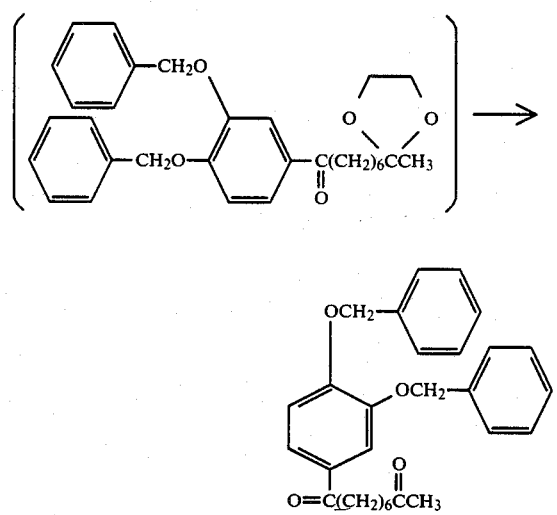

To a mixture of 12.7 g of 3,4-dibenzyloxybenzaldehyde and 150 ml of tetrahydrofuran was added dropwise an ether solution of Grignard reagent prepared from 10.4 g of 2-methyl-2-(6-bromohexyl)-1,3-dioxolane and 1.1 g of magnesium at a temperature below 5° C. After stirring the mixture for 2 hours at room temperature, water was added to the mixture and acidifying the mixture by the addition of diluted hydrochloric acid, the reaction mixture thus obtained was extracted with toluene. The extract was washed with water, dried by anhydrous magnesium sulfate, and concentrated under reduced pressure. To the residue were added 300 ml of acetone and 0.1 g of p-toluenesulfonic acid, the mixture was stirred overnight at room temperature and concentrated under reduced pressure. The residue was extracted with toluene and the extract was washed with an aqueous 5% sodium hydrogencarbonate solution, washed with water, dried over anhydrous magnesium sulfate, and concentrated under reduced pressure to provide an oily product. The product was applied to silica gel (500 ml) column chromatography and eluted with a mixture of toluene and ethyl acetate (19:1) to provide 4.4 g of 1-(3,4-dibenzyloxyphenyl)-1,8-nonanedione. Melting point 64°-66° C.

REFERENCE EXAMPLE 26

(Raw material in Example 32)

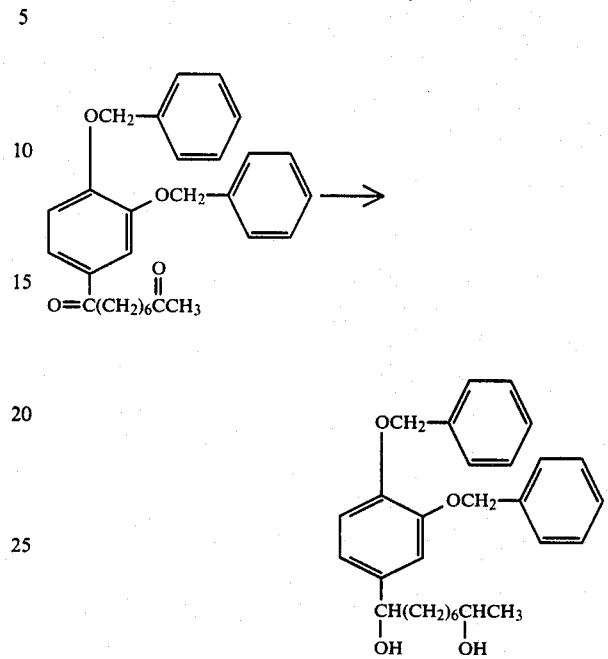

A mixture of 0.8 g of 1-(3,4-dibenzyloxyphenyl)-1,8-nonanedione and 10 ml of tetrahydrofuran was added to a solution of 0.1 g of lithium aluminum hydride in 50 ml of ether under ice-cooling followed by stirring for 2 hours at room temperature. Then, 50 ml of toluene was added to the reaction mixture and the mixture was acidified by the addition of diluted hydrochloric acid. The toluene layer was collected, washed with an aqueous 5% sodium hydrogencarbonate solution, washed with water, dried over anhydrous magnesium carbonate, and concentrated under reduced pressure to provide 0.8 g of 1-(3,4-dibenzyloxyphenyl)-1,8-nonanediol as an oil.

Nuclear magnetic resonance spectra (in CDCl$_3$, TMS, ppm): 1.05–1.80(15H), 3.8–4.0(1H), 4.56(1H), 5.18(2H), 5.20(2H), 6.80–7.60(13H).

REFERENCE EXAMPLE 27

(Raw material in Example 33)

(a) 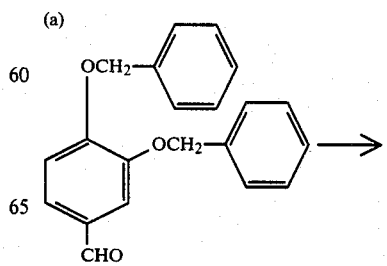

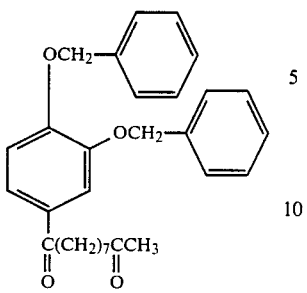

By following the procedure as in Reference Example 25 using a Grignard reagent prepared from 3 g of 3,4-dibenzyloxybenzaldehyde, 2.5 g of 2-methyl-(7-bromoheptyl)-1,3-dioxolane, and 0.3 g of magnesium, 0.8 g of 1-(3,4-dibenzyloxyphenyl)-1,9-decanedione was obtained.

Melting point 72°–74° C.

(b)

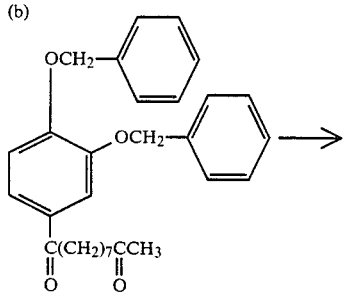

By following the prodecure as in Reference Example 26 using 1 g of 1-(3,4-dibenzyloxyphenyl)-1,9-decanedione as the raw material, 1.0 g of 1-(3,4-dibenzyloxyphenyl)-1,9-decanediol was obtained. Melting point 66° C.

REFERENCE EXAMPLE 28

(Raw material in Example 34)

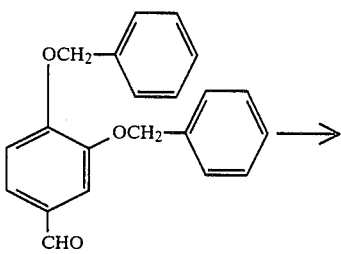

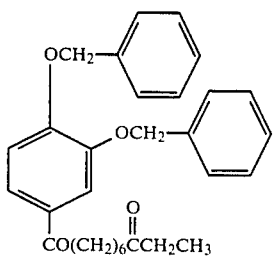

By following the procedure as in Reference Example 25 using 8 g of 3,4-dibenzyloxybenzaldehyde, and a Grignard reagent prepared from 8 g of 2-ethyl-2-(6-bromohexyl)-1,3-dioxsolane, and 850 mg of magnesium, 2 g of 1-(3,4-dibenzyloxyphenyl)-1,8-decanedione was obtained.

Melting point 67°–68° C.

REFERENCE EXAMPLE 29

(Raw material in Example 35)

(a)

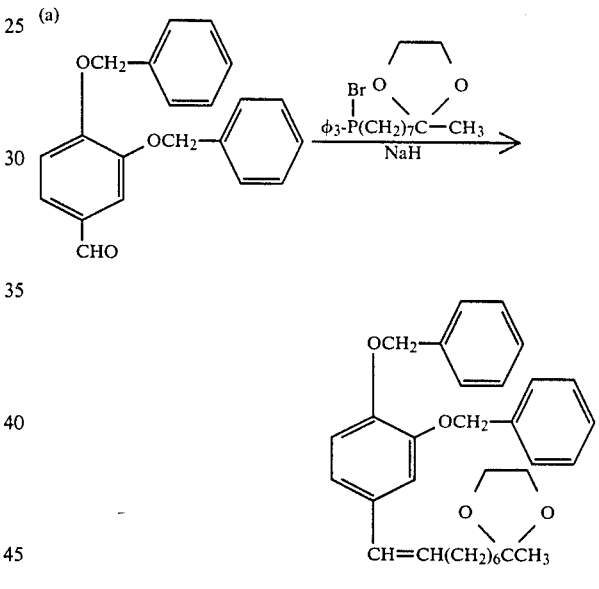

A mixture of 640 mg of oily sodium hydride (60%) and 10 mg of dimethyl sulfoxide was stirred for 45 minutes at 75° to 80° C. After cooling the mixture, a mixture of 50 ml of dimethyl sulfoxide and 8.2 g of 8-ethylenedioxynonyl triphenylphosphonium bromide prepared from 2-methyl-2-(7-bromoheptyl)-1,3-dioxolan and triphenylphosphin was added to the mixture. After 10 minutes, a mixture of 2.5 g of 3.4-dibenzyloxybenzaldehyde and 10 ml of dimethyl sulfoxide was added to the mixture at room temperature and the resultant mixture was stirred overnight. To the reaction mixture was added 500 ml of water and the product was extracted with ether. The extract was washed with water, dried over anhydrous magnesium sulfate, and concentrated under reduced pressure to provide an oily product. The product was applied to the silica gel (200 ml) column chromatography and eluted with a mixture of n-hexane and ether (1:1) to provide 1.4 g of 1-(3,4-dibenzyloxyphenyl)-9-ethylenedioxy-1-decene.

Nuclear magnetic resonance spectra (in CDCl$_3$, TMS, ppm): 1.05–1.8(11H), 1.9–2.4(2H), 3.85(4H), 5.05(4H), 6.0–7.5(15H).

(b)

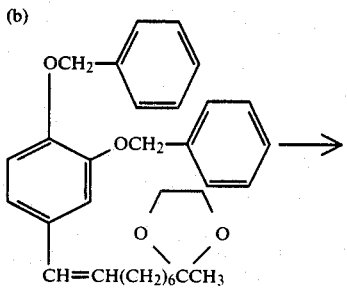

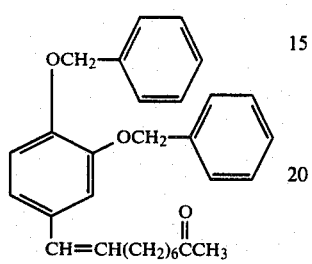

A mixture of 1.4 g of 1-(3,4-dibenzyloxyphenyl)-9-ethylenedioxy-1-decene, 50 ml of acetone, and 50 mg of p-toluenesulfonic acid was stirred overnight at room temperature. After adding thereto 50 mg of sodium carbonate, the reaction mixture was concentrated under reduced pressure, and after adding thereto 50 ml of water, the product was extracted with toluene. The extract was washed with water, dried over anhydrous magnesium sulfate, and concentrated under reduced pressure to provide 1.1 g of 1-(3,4-dibenzyloxyphenyl)-1-decen-9-one as an oil.

Nuclear magnetic resonance spectra (in CDCl$_3$, TMS, ppm): 1.05–1.8(8H), 2.1(3H), 2.1–2.6(4H), 5.16(4H), 6.0–7.6(15H).

REFERENCE EXAMPLE 30

(Raw material in Example 36)

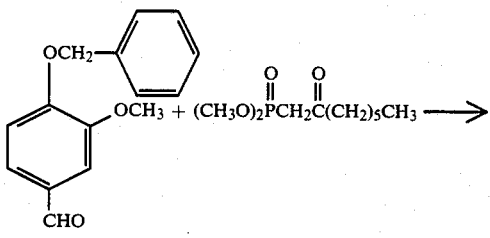

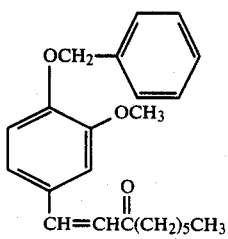

By following the procedure as in Reference Example 1(a) using 1.2 g of 4-benzyloxy-3-methoxybenzaldehyde and 1.53 g of dimethyl 2-oxooctylphosphonate, 1.27 g of 1-(4-benzyloxy-3-methoxyphenyl)-1-nonen-3-one was obtained. Melting point 78°–81° C.

REFERENCE EXAMPLE 31

(Raw material in Example 37)

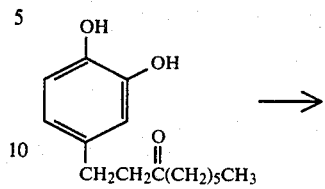

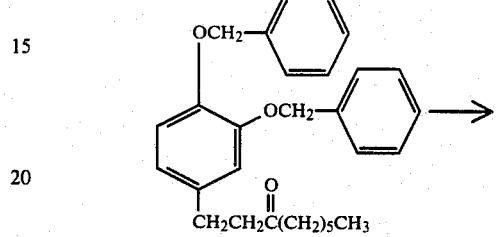

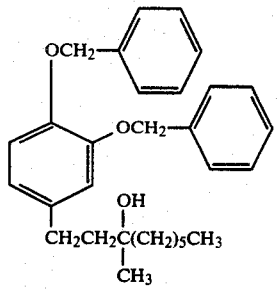

(a) To a solution of 1.2 g of 1-(3,4-dihydroxyphenyl)-3-nonanone in 10 ml of dimethylformamide was added 200 mg of oily sodium hydride (60%) and after stirring the mixture for 15 minutes at room temperature, 0.9 g of benzyl bromide was added to the mixture followed by stirring for 15 minutes at room temperature. After further adding thereto 200 mg of oily sodium hydride (60%) and stirring the mixture for 15 minutes at room temperature, 0.9 g of benzyl bromide was added to the mixture followed by stirring for 1.5 hours at room temperature. After adding 50 ml of water to the reaction mixture, the product was extracted with toluene. The extract was washed with water, dried over anhydrous magnesium sulfate, and then the solvent was distilled off under reduced pressure. The residue was applied to silica gel column chromatography and eluted with toluene to provide 1.8 g of 1-(3,4-dibenzyloxyphenyl)-3-nonanone as a sticky product.

Nuclear magnetic resonance spectra (in CDCl$_3$, TMS, ppm): 0.87(3H, —CH$_3$), 1.05–1.8(8H, —(CH$_2$)$_4$—), 1.30(2H, —CH$_2$—), 2.55–2.85(4H,

5.07(4H, —OCH$_2$×2), 6.5–7.5(13H).

(b) A solution of 1.75 g of 1-(3,4-dibenzyloxyphenyl)-3-nonanone in 10 ml of tetrahydrofuran was cooled to 0° to 5° C. and then an ether solution of a Grignard reagent prepared from 0.24 g of metallic magnesium and 1.7 g of methyl iodide was added dropwise to the mixture. Thereafter, the resultant mixture was stirred for 15 minutes and after adding thereto 50 ml of an aqueous 5% hydrochloric acid solution, the product was extracted with toluene. The extract was washed with water, dried over anhydrous magnesium sulfate, and the solvent was distilled off under reduced pressure to provide 1.6 g of 1-(3,4-dibenzyloxyphenyl)-3-methyl-3-nonanol.

Nuclear magnetic resonance spectra (in CDCl₃, TMS, ppm): 0.88(3H, —CH₃), 1.1–1.9(15H,

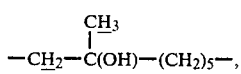

[1.18(3H, —CH₃)]), 2.4–2.8(2H, —CH₂—), 5.08(4H, —OCH₂—×2), 6.5–7.6(13H).

REFERENCE EXAMPLE 32

(Raw material in Example 38)

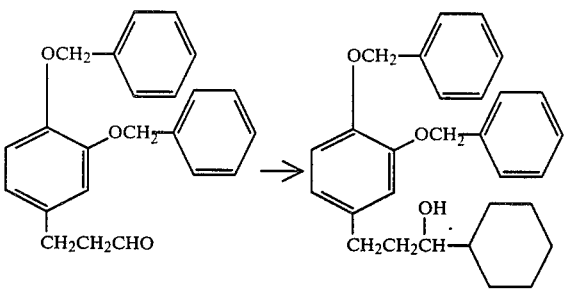

A solution of 0.4 g of 3-(3,4-dibenzyloxyphenyl)propionaldehyde in 5 ml of anhydrous tetrahydrofuran was cooled to 0° to 5° C. and then 5 ml of an ether solution of cyclohexyl magnesium bromide prepared from 0.12 g of metallic magnesium and 0.82 g of cyclohexyl bromide was added dropwise to the solvent. Thereafter, the reaction mixture was stirred for 15 minutes and after adding thereto 50 ml of an aqueous 5% hydrochloric acid solution, the product was extracted with 30 ml of toluene. The extract was washed with water, dried over anhydrous magnesium sulfate, and the solvent was distilled off under reduced pressure to provide an oily product. The product was applied to silica gel column chromatography and eluted with toluene to provide 0.2 g of 3-(3,4-dibenzyloxyphenyl)-1-cyclohexyl-1-propanol.

Melting point 107°–108° C.

| Elemental analysis for C₂₉H₃₀O₃: | | |
| --- | --- | --- |
| | C | H |
| Calculated: | 80.89% | 7.96% |
| Found: | 80.88% | 8.15% |

EXAMPLE 1

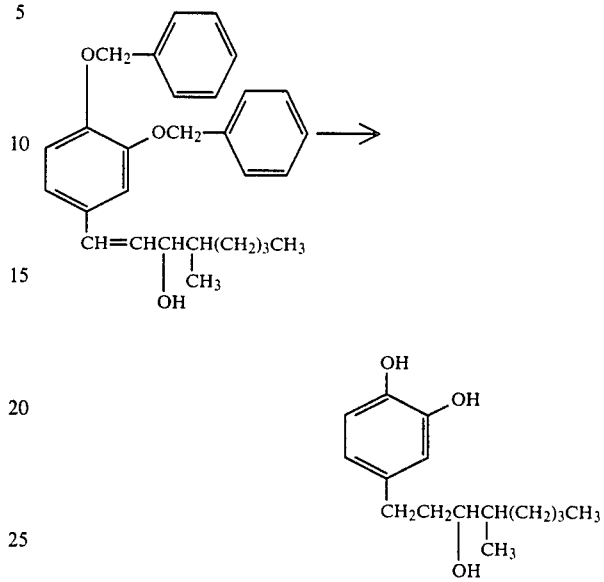

In 20 ml of ethanol was dissolved 0.4 g of 1-(3,4-dibenzyloxyphenyl)-4-methyl-1-octen-3-ol and the compound thus dissolved was catalytically reduced using 0.1 g of 10% palladium-carbon as a catalyst until the absorption of hydrogen stopped. After the reduction was over, the catalyst was filtered off and the filtrate was concentrated under reduced pressure to provide 0.23 g of 1-(3,4-dihdyroxyphenyl)-4-methyl-3-octanol.

Nuclear magnetic resonance spectra (in CDCl₃, TMS internal standard, ppm): 0.7–1.8(15H), 2.57(2H), 3.45(1H), 6.4–6.8(3H).

EXAMPLE 2

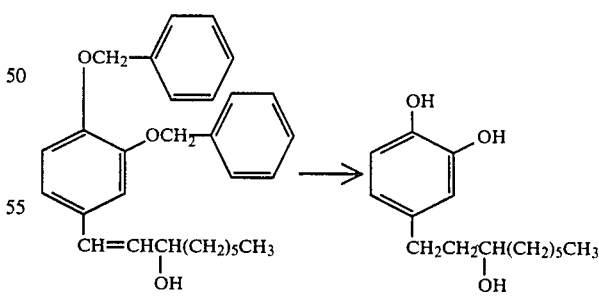

By following the same procedure as in Example 1 using 0.85 g of 1-(3,4-dibenzyloxyphenyl)-1-nonen-3-ol, 0.4 g of 1-(3,4-dihydroxyphenyl)-3-nonanol was obtained.

Nuclear magnetic resonance spectra (in CDCl₃, TMS internal standard, ppm): 0.8–1.9(15H), 2.55(2H), 3.60(1H), 6.4–6.8(3H).

EXAMPLE 3

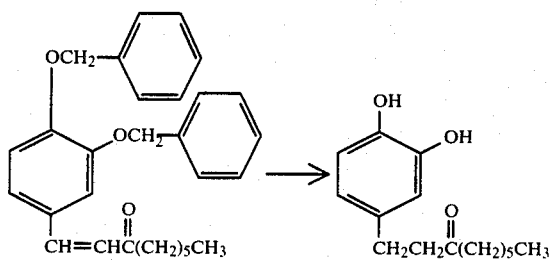

Using 0.2 g of 10% palladium-carbon as catalyst, 0.5 g of 1-(3,4-dibenzyloxyphenyl)-1-nonen-3-one was catalytically reduced in a mixture of 10 ml of methanol and 10 ml of ethyl acetate until the absorption of hydrogen stopped. Then, the catalyst was filtered off and the filtrate was concentrated under reduced pressure. The residue was applied to silica gel column chromatography and eluted with a mixture of toluene and ethyl acetate (10:1) to provide 0.2 g of white crystals of 1-(3,4-dihydroxyphenyl)-3-nonanone.

Melting point 50°–53° C.

| Elemental analysis for $C_{15}H_{22}O_3$: | | |
|---|---|---|
| | C | H |
| Calculated: | 71.97% | 8.86% |
| Found: | 71.66% | 8.77% |

EXAMPLE 4

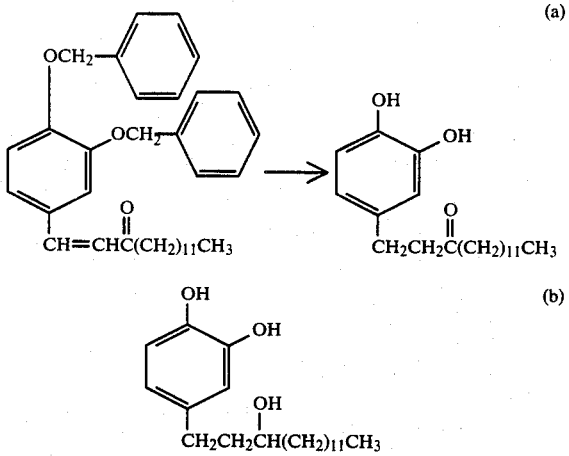

In a mixture of 30 ml of ethyl acetate and 5 ml of ethanol was dissolved 1.5 g of 1-(3,4-dibenzyloxyphenyl)-1-pentadecen-3-one and the compound was catalytically reduced using 0.2 g of 10% palladium-carbon as a catalyst until the absorption of hydrogen stopped. Then, the catalyst was filtered off and the filtrate was concentrated under reduced pressure. The residue was applied to silica gel (80 ml) column chromatography and eluted with a mixture of toluene and ethyl acetate (10:1) to provide 0.55 g of white crystals of 1-(3,4-dihydroxyphenyl)-3-pentadecanone (a) as the eluate first merging from the column.

Melting point 67°–68° C.

| Elemental analysis for $C_{21}H_{34}O_3$: | | |
|---|---|---|
| | C | H |
| Calculated: | 75.41% | 10.24% |
| Found: | 75.12% | 10.38% |

After the elution of 1-(3,4-dihydroxyphenyl)-3-pentadecanone was over, further elution was carried out with toluene to provide 0.1 g of 1-(3,4-dihydroxyphenyl)-3-pentadecanol (b) as a white crystals.

Melting point 63°–64° C.

| Elemental analysis for $C_{21}H_{36}O_3$: | | |
|---|---|---|
| | C | H |
| Calculated: | 74.95% | 10.78% |
| Found: | 74.88% | 10.81% |

By following the procedure as in Example 4, the compounds in following Examples 5 to 8 were prepared.

EXAMPLE 5

(Using the compound obtained in Reference Example 4)

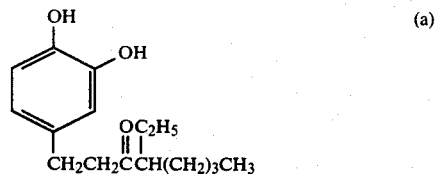

1-(3,4-Dihydroxyphenyl)-4-ethyl-3-octanone (a).

Oily product.

Nuclear magnetic resonance spectra (in CDCl$_3$, TMS internal standard, ppm): 0.6–1.8(14H), 2.3(1H), 2.67(4H), 6.4–6.8(3H).

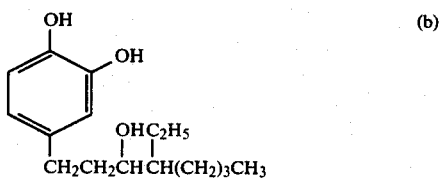

1-(3,4-Dihydroxyphenyl)-4-ethyl-3-octanol (b).

Oily product.

Nuclear magnetic resonance spectra (in CDCl$_3$, TMS internal standard, ppm): 0.85(6H), 1.1–1.9(11H), 2.67(2H), 3.63(1H), 6.4–6.7(3H).

EXAMPLE 6

(Using the compound obtained in Reference Example 5)

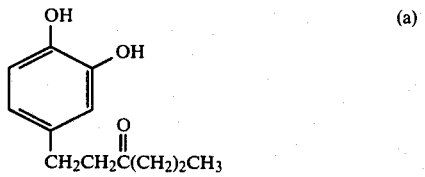

1-(3,4-Dihydroxyphenyl)-3-hexanone (a).

Melting point 37°–39° C.

| Elemental analysis for $C_{12}H_{16}O_3$: | | |
|---|---|---|
| | C | H |
| Calculated: | 69.21% | 7.74% |
| Found: | 68.94% | 7.91% |

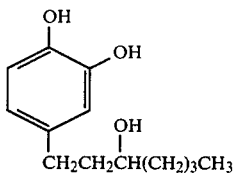 (b)

1-(3,4-Dihydroxyphenyl)-3-hexanol (b).
Oily product.
Nuclear magnetic resonance spectra (in CDCl₃, TMS internal standard, ppm): 0.9(3H), 1.1–1.9(6H), 2.6(2H), 3.65(1H), 6.6–6.9(3H).

EXAMPLE 7

(Using the compound obtained in Reference Example 6)

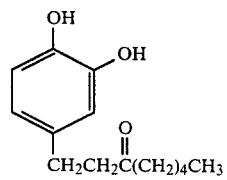 (a)

1-(3,4-Dihydroxyphenyl)-3-octanone (a).
Melting point 53°–55° C.

| Elemental analysis for $C_{14}H_{20}O_3$: | | |
|---|---|---|
| | C | H |
| Calculated: | 71.16% | 8.53% |
| Found: | 70.87% | 8.74% |

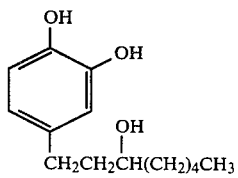 (b)

1-(3,4-Dihydroxyphenyl)-3-octanol (b).
Oily product.
Nuclear magnetic resonance spectra (in CDCl₃, TMS internal standard, ppm): 0.9(3H), 1.1–1.9(10H), 2.6(2H), 3.65(1H), 6.5–6.9(3H).

EXAMPLE 8

(Using the compound obtained in Reference Example 7)

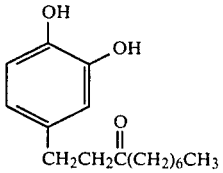 (a)

1-(3,4-Dihydroxyphenyl)-3-decanone (a)
Melting point 65°–66° C.

| Elemental analysis for $C_{16}H_{24}O_3$: | | |
|---|---|---|
| | C | H |
| Calculated: | 72.69% | 9.15% |
| Found: | 72.42% | 9.48% |

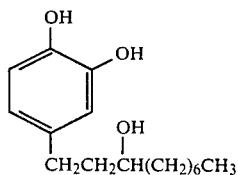 (b)

1-(3,4-Dihydroxyphenyl)-3-decanol (b).
Oily product.
Nuclear magnetic resonance spectra (in CDCl₃, TMS internal standard, ppm): 0.9(3H), 1.1–1.9(14H), 2.6(2H), 3.65(1H), 6.5–6.9(3H).

By following the procedure as in Example 1, the compounds of following Examples 9 to 11 were prepared.

EXAMPLE 9

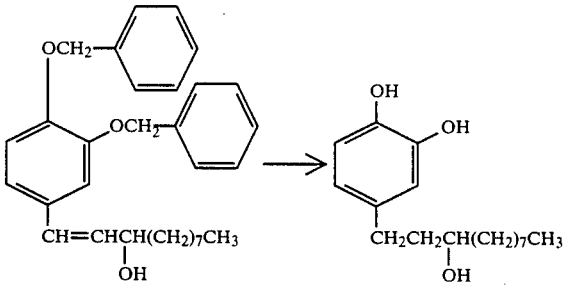

1-(3,4-Dihydroxyphenyl)-3-undecanol.
Melting point 45°–47° C.

| Elemental analysis for $C_{17}H_{28}O_3$: | | |
|---|---|---|
| | C | H |
| Calculated: | 72.82% | 10.06% |
| Found: | 72.76% | 10.29% |

EXAMPLE 10

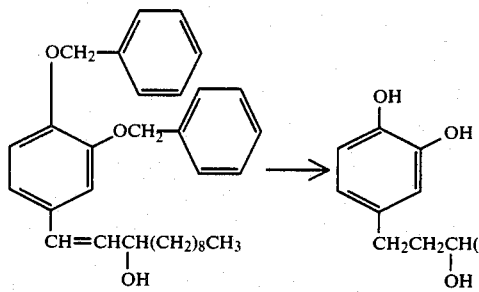

1-(3,4-Dihydroxyphenyl)-3-dodecanol.

Melting point 53°-55° C.

| Elemental analysis for $C_{18}H_{30}O_3$: | | |
|---|---|---|
| | C | H |
| Calculated: | 73.43% | 10.27% |
| Found: | 73.48% | 10.47% |

EXAMPLE 11

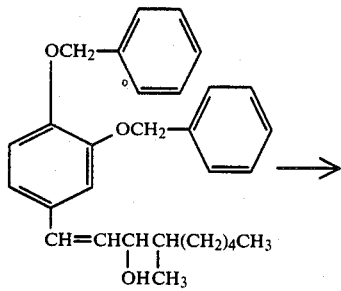

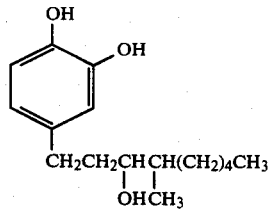

1-(3,4-Dihydroxyphenyl)-4-methyl-3-nonanol.

Oily product.

Nuclear magnetic resonance spectra (in CDCl$_3$, TMS internal standard, ppm): 0.7-1.9(17H), 2.58(2H), 3.55(1H), 6.5-6.9(3H), By following the same procedure as in Example 3, the compound of following Example 12 was prepared.

EXAMPLE 12

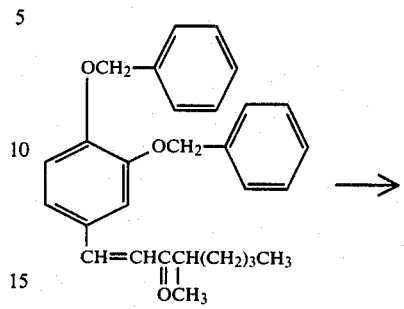

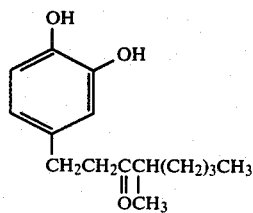

1-(3,4-Dihydroxyphenyl)-4-methyl-3-octanone.

Oily product.

Nuclear magnetic resonance spectra (in CDCl$_3$, TMS internal standard. ppm): 0.6-1.8(12H), 2.5(1H), 2.74(4H), 6.4-6.8(3H)

EXAMPLE 13

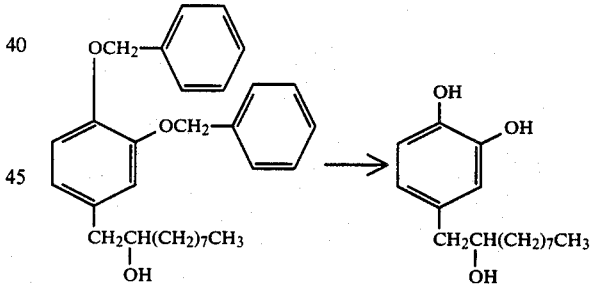

In 10 ml of ethanol was dissolved 0.5 g of 1-(3,4-dibenzyloxyphenyl)-2-decanol and the compound was catalytically reduced using 0.2 g of 10% palladium-carbon at room temperature and under atomospheric until the absorption of hydrogen stopped. After the reaction was over, the catalyst was filtered off and the filtrate was concentrated under reduced pressure to provide 0.28 g of 1-(3,4-dihydroxyphenyl)-2-decanol. Oily product.

Nuclear magnetic resonance spectra (in CDCl$_3$, TMS internal standard, ppm): 0.89(3H, —CH$_3$), 1.1-1.7(14H, —(CH$_2$)$_7$—), 1.62(2H, —CH$_2$—), 3.74(1H, —<u>CH</u>(OH)—), 6.4-6.9(3H, H of benzene ring).

EXAMPLE 14

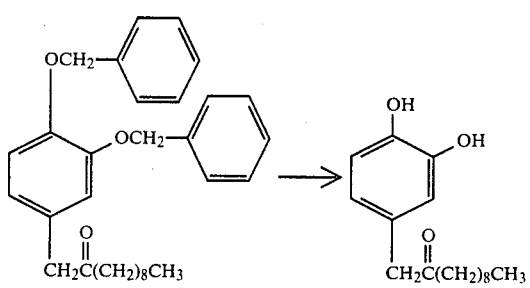

By following the same procedure as in Example 13 using 0.3 g of 1-(3,4-dibenzyloxyphenyl)-2-undecanone, 140 mg of 1-(3,4-dihydroxyphenyl)-2-undecanone was obtained. Oily product.

Nuclear magnetic resonance spectra (in CDCl$_3$, TMS internal standard, ppm): 0.86(3H, —CH$_3$), 1.0–1.7(14H, —(CH$_2$)$_7$—), 2.47(2H, —CH$_2$—), 3.56(2H, —CH$_2$—), 6.6–6.9(3H, H of benzene ring).

EXAMPLE 15

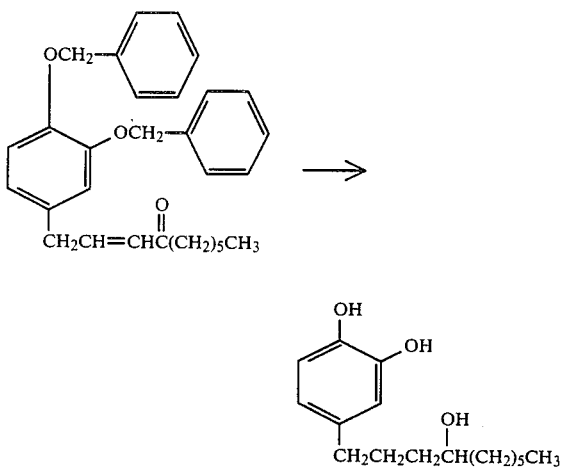

By following the same procedure as in Example 4 using 0.3 g of 1-(3,4-dibenzylophenyl)-2-decen-4-one, 0.1 g of 1-(3,4-dihydroxyphenyl)-4-decanol was obtained.

Oily product.

Nuclear magnetic resonance spectra (in CDCl$_3$, TMS internal standard, ppm): 0.86(3H, —CH$_3$), 1.1–1.8(14H), 1.48(2H, —CH$_2$—), 3.61(1H,

6.4–6.8(3H, H of benzene ring).

EXAMPLE 16

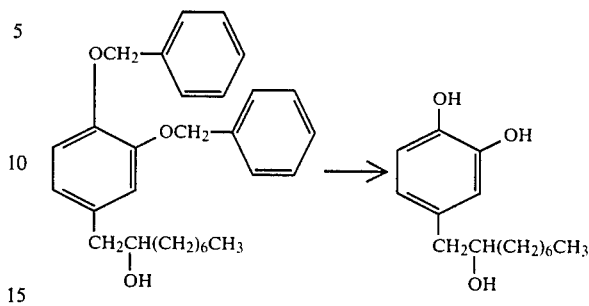

By following the same procedure as in Example 13 using 0.5 g of 1-(3,4-dibenzyloxyphenyl)-2-nonanol, 0.27 g of 1-(3,4-dihydroxyphenyl)-2-nonanol was obtained. Oily product.

Nuclear magnetic resonance spectra (in CDCl$_3$, TMS internal standard, ppm): 0.89(3H, —CH$_3$), 1.1–1.7(12H, —(CH$_2$)$_6$—), 1.62(2H, —CH$_2$—), 3.75(1H, —C$\underline{H}$(OH)—), 6.4–6.9(3H, H of benzene ring).

EXAMPLE 17

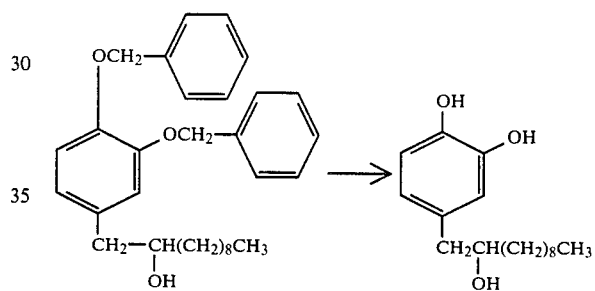

By following the same procedure as in Example 13 using 0.5 g of 1-(3,4-dibenzyloxyphenyl)-2-undecanol, 0.29 g of 1-(3,4-dihydroxyphenyl)-2-undecanol was obtained.

Melting point 56°–58° C.

| Elemental analysis for C$_{17}$H$_{28}$O$_3$: | | |
|---|---|---|
| | C | H |
| Calculated: | 72.82% | 10.06% |
| Found: | 72.70% | 10.26% |

EXAMPLE 18

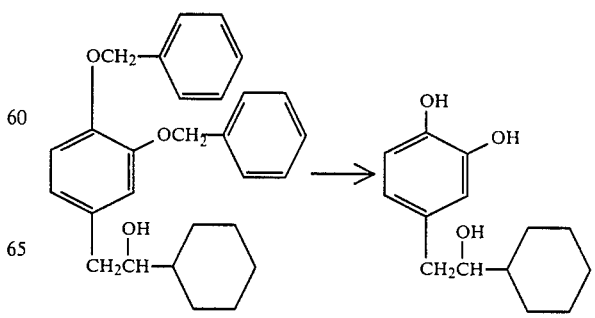

By following the same procedure as in Example 13 using 0.15 g of 2-(3,4-dibenzyloxyphenyl)-1-cyclohexyl-1-ethanol, 0.06 g of 2-(3,4-dihdyroxyphenyl)-1-cyclohexyl-1-ethanol was obtained.

Melting point 106°–108° C.

| Elemental analysis for C<sub>14</sub>H<sub>20</sub>O<sub>3</sub>: | | |
|---|---|---|
| | C | H |
| Calculated: | 71.16% | 8.53% |
| Found: | 70.99% | 8.61% |

EXAMPLE 19

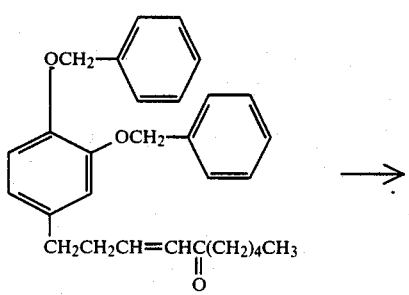

By following the same procedure as in Example 4 using 0.54 g of 1-(3,4-dibenzyloxyphenyl)-3-decen-5-one, 0.28 g of 1-(3,4-dihydroxyphenyl)-5-decanone was obtained.

Melting point 76°–78° C.

| Elemental analysis for C<sub>16</sub>H<sub>24</sub>O<sub>3</sub>: | | |
|---|---|---|
| | C | H |
| Calculated: | 72.14% | 9.84% |
| Found: | 72.18% | 9.75% |

EXAMPLE 20

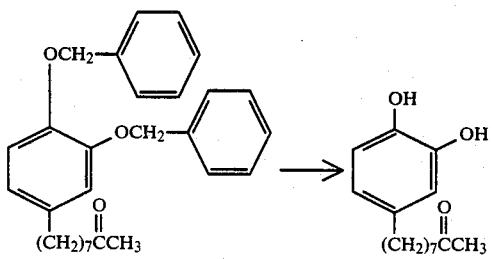

By following the same procedure as in Example 13 using 0.3 g of 9-(3,4-dibenzyloxyphenyl)-2-nonanone, 0.16 g of 9-(3,4-dihydroxyphenyl)-2-nonanone was obtained. Oily product.

Nuclear magnetic resonance spectra (in CDCl<sub>3</sub>, TMS internal standard, ppm): 1.0–1.80(10H), 2.16(3H), 2.30–2.60(4H), 6.50–6.90(3H).

EXAMPLE 21

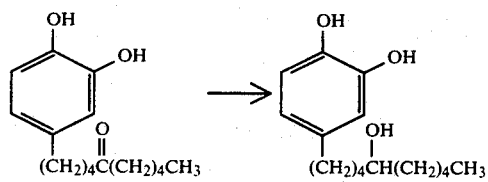

In 1.5 ml of methanol was dissolved 150 mg of 1-(3,4-dihydroxyphenyl)-5-decanone and 20 mg of sodium borohydride was added to the solution under ice-cooling followed by stirring for 30 minutes. Then, the solvent was distilled off from the reaction mixture and after adding 10 ml of water to the residue thus formed, the product was extracted with ether. The extract was dried over anhydrous magnesium sulfate and the solvent was distilled off to provide white crystals of 1-(3,4-dihydroxyphenyl)-5-decanol, which was collected by filtration with the addition of n-hexane. Yield 117 mg.

| Elemental analysis for C<sub>16</sub>H<sub>26</sub>O<sub>3</sub>: | | |
|---|---|---|
| | C | H |
| Calculated: | 72.14% | 9.84% |
| Found: | 72.18% | 9.75% |

EXAMPLE 22

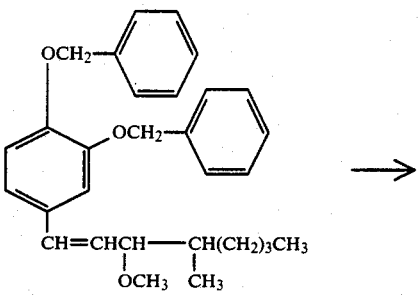

Using 0.1 g of 10% palladium-carbon as catalyst, 560 mg of 1-(3,4-dibenzyloxyphenyl)-3-methoxy-4-methyl-1-octene was catalytically reduced in a mixture of 5 ml of methanol and 5 ml of ethyl acetate until the absorption of hydrogen stopped. Thereafter, the catalyst was filtered off and the filtrate was concentrated under reduced perssure to provide 330 mg of oily 1-(3,4-dihydroxyphenyl)-3-methoxy-4-methyl-octane.

Nuclear magnetic resonance spectra (in CDCl<sub>3</sub>, TMS internal standard, ppm): 0.7–1.9(5H), 2.52(2H), 3.05(1H), 3.40(3H), 6.5–6.9(3H).

EXAMPLE 23

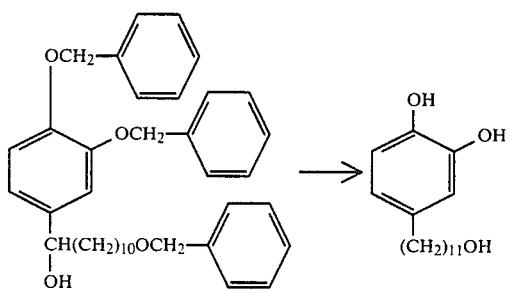

In 40 ml of acetic acid was dissolved 4.4 g of 11-benzyloxy-1-(3,4-dibenzyloxyphenyl)-1-undecanol and the compound was catalytically reduced in the presence of 1 g of 10% palladium-carbon at room temperature and under atmospheric pressure until the absorption of hydrogen stopped. After the reaction was over, the catalyst was filtered off and after adding 300 ml of water to the filtrate, the product was extracted twice each time with 70 ml of ethyl acetate. The extract was washed with water, dried over anhydrous magnesium sulfate, and then the solvent was distilled off to provide a solid product. The solid product was recrystallized from 10 ml of a mixture of ethyl acetate and toluene (1:1) to provide 1.5 g of 11-(3,4-dihydroxyphenyl)-1-undecanol.

Melting point 92°–93° C.

| Elemental analysis for $C_{17}H_{28}O_3$: | | |
| --- | --- | --- |
| | C | H |
| Calculated: | 72.82% | 10.06% |
| Found: | 73.06% | 10.29% |

By following the procedure as in Example 23, the compounds of following Examples 24 and 25 A, B were prepared.

EXAMPLE 24

(Using the compound obtained in Reference Example 18 step (b))

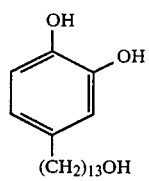

13-(3,4-Dihydroxyphenyl)-1-tridecanol.
Melting point 93°–95° C.

| Elemental analysis for $C_{19}H_{32}O_3$: | | |
| --- | --- | --- |
| | C | H |
| Calculated: | 73.98% | 10.46% |
| Found: | 73.73% | 10.75% |

EXAMPLE 25 A (Using the compound obtained in Reference Example 19 A step (b))

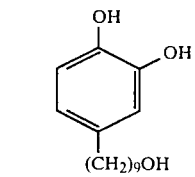

9-(3,4-Dihydroxyphenyl)-1-nonanol.
Melting point 89°–91° C.

| Elemental analysis for $C_{15}H_{24}O_3$: | | |
| --- | --- | --- |
| | C | H |
| Calculated: | 71.39% | 9.59% |
| Found: | 71.12% | 9.80% |

EXAMPLE 25 B (Using the compound obtained in Reference Example 19 B step (b))

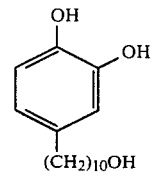

10-(3,4-Dihydroxyphenyl)-1-decanol.
Melting point 89°–91° C.

| Elemental analysis for $C_{16}H_{26}O_3$: | | |
| --- | --- | --- |
| | C | H |
| Calculated: | 72.14% | 9.84% |
| Found: | 71.96% | 10.11% |

EXAMPLE 26

(Using the compound obtained in Reference Example 20)

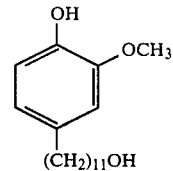

By following the procedure as in Example 23, 11-(4-hydroxy-3-methoxyphenyl)-1-undecanol was obtained. Melting point 72°–74° C.

| Elemental analysis for $C_{18}H_{30}O_3$: | | |
| --- | --- | --- |
| | C | H |
| Calculated: | 73.33% | 10.27% |
| Found: | 73.09% | 10.26% |

EXAMPLE 27

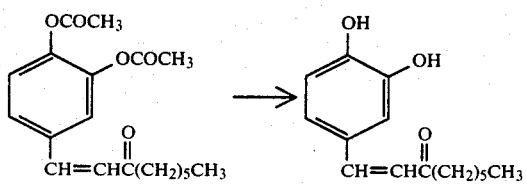

In 10 ml of methanol was dissolved 830 mg of 1-(3,4-diacetoxyphenyl)-1-nonen-3-one and after adding 7.5 ml of an aqueous 1N-sodium hydroxide solution to the solution, the mixture was stirred for 30 minutes at room temperature. Then, the reaction mixture was ice-cooled and after adding thereto 25 ml of water, the mixture was acidified with the addition of 5 ml of an aqueous 1N-hydrochloric acid solution to form crystals, which were collected by filtration and washed with water to provide 580 mg of 1-(3,4-dihydroxyphenyl)-1-nonen-3-one.

Melting point 114°–115° C.

| Elemental analysis for $C_{15}H_{20}O_3$: | | |
|---|---|---|
| | C | H |
| Calculated: | 72.55% | 8.12% |
| Found: | 72.32% | 8.23% |

EXAMPLE 28

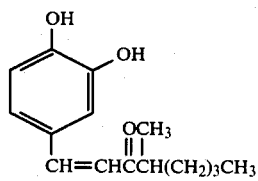

A hydrochloric acid-acidified aqueous solution obtained by following the same procedure as in Example 27 using 1.0 g of 1-(3,4-diacetoxyphenyl)-4-methyl-1-octen-3-one, was extracted twice each time with 20 ml of ether. The extract was washed with water, dried over anhydrous magnesium sulfate, and concentrated under reduced pressure to provide 0.7 g of oily 1-(3,4-dihydroxyphenyl)-4-methyl-1-octen-3-one.

Nuclear magnetic resonance spectra (in CDCl₃, TMS internal standard, ppm): 0.88(3H), 1.05–1.9(9H), 2.85(1H), 6.59–7.7(5H).

EXAMPLE 29

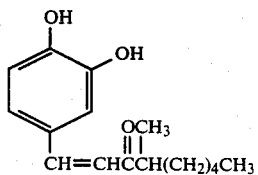

By following the same procedure as in Example 28 using 1.0 g of 1-(3,4-diacetoxyphenyl)-4-methyl-1-nonen-3-one, 0.7 g of 1-(3,4-dihydroxyphenyl)-4-methyl-1-nonen-3-one was obtained as an oil.

Nuclear magnetic resonance spectra (in CDCl₃, TMS internal standard, ppm): 0.88(3H), 1.05–1.9(11H), 2.84(1H), 6.59–7.7(5H).

EXAMPLE 30

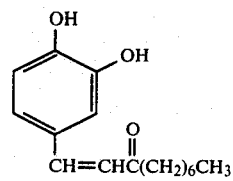

By following the same procedure as in Example 27 using 0.25 g of 1-(3,4-diacetoxyphenyl)-1-decen-3-one, 0.14 g of 1-(3,4-dihydroxyphenyl)-1-decen-one was obtained.

Melting point 116°–118° C.

| Elemental analysis for $C_{16}H_{22}O_3$: | | |
|---|---|---|
| | C | H |
| Calculated: | 73.25% | 8.45% |
| Found: | 73.30% | 8.71% |

EXAMPLE 31

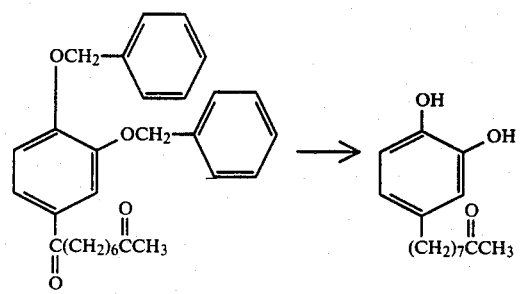

Using 0.5 g of 10% palladium-carbon, 3.2 g of 1-(3,4-dibenzyloxyphenyl)-1,8-nonanedione was catalytically reduced in a mixture of 50 ml of ethanol and 1.5 ml of an aqueous 5% perchloric acid solution at room temperature and under atomospheric pressure until the absorption of hydrogen stopped. After the reaction was over, the catalyst was filtered off and the filtrate was concentrated under reduced pressure. The residue was applied to silica gel (50 ml) column chromatography and eluted with a mixture of toluene and ethyl acetate (4:1). The crystals thus obtained were recrystallized from a mixture of toluene and n-hexane to provide 1-(3,4-dihydroxyphenyl)-8-nonanone.

Melting point 73°–75° C.

| Elemental analysis for $C_{15}H_{22}O_3$: | | |
|---|---|---|
| | C | H |
| Calculated: | 71.97% | 8.86% |
| Found: | 71.91% | 9.12% |

EXAMPLE 32

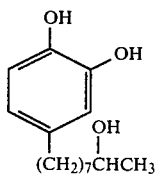

By following the same procedure as in Example 31 using 780 mg of 1-(3,4-dibenzyloxyphenyl)-1,8-nonanediol, 210 mg of 1-(3,4-dihydroxyphenyl)-8-nonanol was obtained.

Melting point 58°–61° C.

Nuclear magnetic resonance spectra (in CDCl$_3$, TMS, ppm): 1.0–1.8(15H), 2.48(2H), 3.84(1H), 6.5–6.9(3H).

EXAMPLE 33

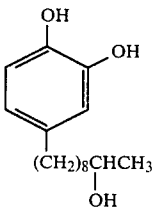

By following the same procedure as in Example 31 using 1 g of 1-(3,4-dibenzyloxyphenyl)-1,9-decanediol, 340 mg of 1-(3,4-dihydroxyphenyl)-9-decanol was obtained.

Melting point 43°–46° C.

Nuclear magnetic resonance spectra (in CDCl$_3$, TMS, ppm): 1.05–1.8(17H), 2.50(2H), 3.86(1H), 6.5–6.9(3H).

EXAMPLE 34

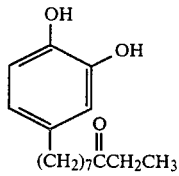

By following the same procedure as in Example 31 using 2 g of 1-(3,4-dibenzyloxyphenyl)-1,8-decanedione as a raw material, 200 mg of 1-(3,4-dihydroxyphenyl)-8-decanone was obtained.

Melting point 76°–78° C.

Nuclear magnetic resonance spectra (in CDCl$_3$, TMS, ppm): 1.04(3H), 1.0–1.8(10H), 2.2–2.6(6H), 6.5–6.9(3H).

EXAMPLE 35

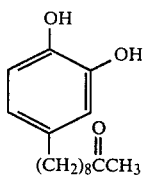

By following the same procedure as in Example 1 using 1.02 g of 1-(3,4-dibenzyloxyphenyl)-1-decen-9-one as a raw material, 450 mg of 1-(3,4-dihydroxyphenyl)-9-decanone was obtained.

Melting point 74°–76° C.

Nuclear magentic resonance spectra (in CDCl$_3$, TMS, ppm): 1.05–1.8(12H), 2.1(3H), 2.3–2.52(4H), 6.5–6.8(3H).

EXAMPLE 36

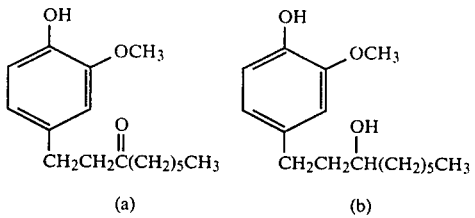

(a)   (b)

By following the same procedure as in Example 4 using 1.2 g of 1-(4-benzyloxy-3-methoxyphenyl)-1-nonen-3-one as a raw material, 660 mg of 1-(4-hydroxy-3-methoxyphenyl)-3-nonanone (a) as an oil and 120 mg of 1-(4-hydroxy-3-methoxyphenyl)-3-nonanol (b) as an oil were obtained.

Nuclear magnetic resonance spectra (in CDCl$_3$, TMS, ppm) of compound (a): 0.9(3H), 1.0–1.8(8H), 2.4(2H), 2.5–3.0(4H), 3.88(3H), 6.5–7.0(3H).

Nuclear magnetic resonance spectra (in CDCl$_3$, TMS, ppm) of compound (b): 0.9(3H), 1.0–2.0(12H), 2.5–2.8(2H), 3.4–3.8(1H), 3.88(3H), 6.6–7.0(3H).

EXAMPLE 37

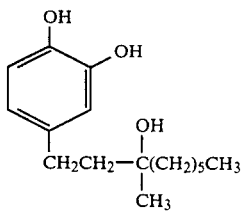

By following the same procedure as in Example 1 using 1.4 g of 1-(3,4-dibenzyloxyphenyl)-3-methyl-3-nonanol, 0.7 g of 1-(3,4-dihydroxyphenyl)-3-methyl-3-nonanol was obtained.

Melting point 81°–83° C.

| Elemental analysis for $C_{16}H_{26}O_3$: | | |
|---|---|---|
| | C | H |
| Calculated: | 72.14% | 9.84% |
| Found: | 71.96% | 10.06% |

EXAMPLE 38

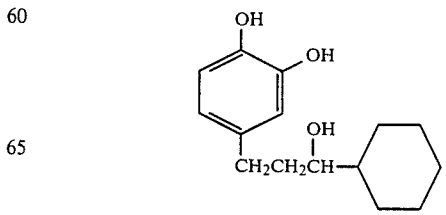

By following the same procedure as in Example 1 using 0.2 g of 3-(3,4-dibenzyloxyphenyl)-1-cyclohexyl-1-propanol 0.1 g of 3-(3,4-dihydroxyphenyl)-1-cyclohexyl-1-propanol was obtained.

Melting point 118°-119° C.

| Elemental analysis for $C_{15}H_{22}O_3$: | | |
|---|---|---|
| | C | H |
| Calculated: | 71.97% | 8.86% |
| Found: | 71.85% | 8.95% |

EXAMPLE 39

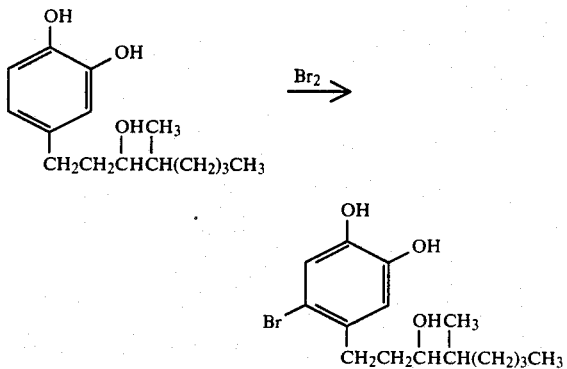

To a solution of 0.5 g of 1-(3,4-dihydroxyphenyl)-4-methyl-3-octanol obtained in Example 1 in 20 ml of acetic acid was added dropwise a mixture of 0.37 g of bromine and 2 ml of acetic acid and after the color of bromine disappeared, the solvent was distilled off under reduced pressure. The residue thus formed was extracted with ethyl acetate. The extract was washed with water, dried over anhydrous magnesium sulfate, and the solvent was distilled off under reduced pressure. The residue was applied to silica gel column chromatography and eluted with a mixture of toluene and ethyl acetate (2:1) to provide 0.5 g of 1-(2-bromo-4,5-dihydroxyphenyl)-4-methyl-3-octanol.

Melting point 68°-71° C.

| Elemental analysis for $C_{15}H_{23}O_3Br$ | | | |
|---|---|---|---|
| | C | H | Br |
| Calculated: | 54.39% | 7.00% | 24.12% |
| Found: | 54.12% | 7.12% | 24.40% |

EXAMPLE 40

(Tablet)

| | |
|---|---|
| 11-(3,4-Dihydroxyphenyl)-1-undecanol (hereinafter, is referred to as "ALT-118") | 50 mg |
| Lactose | 113 mg |
| Corn starch | 28 mg |
| Hydroxypropyl cellulose | 4 mg |
| Calcium carboxymethyl cellulose | 4 mg |
| Magnesium stearate | 1 mg |
| total | 200 mg |

After uniformly mixing 50 g of ALT-118, 113 g of lactose and 28 g of corn starch, 40 ml of a 10% (w/v) aqueous solution of hydroxypropyl cellulose was added to the mixture and the resultant mixture was granulated by a wet granulation method. The granules thus obtained were mixed with 4 g of calcium carboxymethyl cellulose and 1 g of magnesium stearate and the mixture was press-tableted into tablets (200 mg per tablet).

EXAMPLE 41

(Capsule)

| | |
|---|---|
| ALT-118 | 50 mg |
| Crystalline cellulose | 20 mg |
| Crystalline lactose | 129 mg |
| Magnesium stearate | 1 mg |
| total | 200 mg |

The above components each in an amount 1000 times the foregoing amount were mixed and then filled in a gelatin capsule to provide capsules (200 mg per capsule).

EXAMPLE 42

(Inhalation)

After dissolving 0.1 g of ALT-118 in about 90 ml of a mixture of ethanol, propylene glycol and purified water (30:10:60 in weight ratio), the volume of the solution was adjusted to 100 ml using the aforesaid mixture and 10 ml each of the solution was filled in a definite container followed by sealing to provide an inhalation.

What is claimed is:

1. A catechol derivative represented by the formula

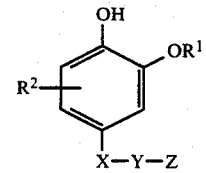

wherein $R^1$ represents a hydrogen atom; $R^2$ represents a hydrogen atom or a halogen atom; X represents a straight chain or branched alkylene group having 1 to 15 carbon atoms or a vinylene group; Y represents a carbonyl group or a group represented by

(wherein $R^3$ and $R^4$, which may be the same or different, each represents a hydrogen atom or a lower alkyl group) and Z represents a hydrogen atom, a straight chain or branched alkyl group having 1 to 15 carbon atoms or a cycloalkyl group; the sum of the carbon atoms of said X and Z being at least 7.

2. The compound as claimed in claim 1 wherein the compound is 11-(3,4-dihydroxyphenyl)-1-undecanol.

3. The compound as claimed in claim 1 wherein the compound is 10-(3.4-dihydroxyphenyl)-1-decanol.

4. The compound as claimed in claim 1 wherein the compound is 1-(3,4-dihydroxyphenyl)-3-undecanol.

5. The compound as claimed in claim 1 wherein the compound is 9-(3,4-dihydroxyphenyl)-2-nonanone.

6. The compound as claimed in claim 1 wherein the compound is 1-(3,4-dihydroxyphenyl)-4-methyl-3-octanol.

7. A pharmaceutical composition for inhibiting the production and release of slow reacting substance of anaphylaxis (SRS-A) comprising a pharmaceutically effective amount of the compound of claim 1 and a pharmaceutically acceptable carrier.

8. A pharmaceutical composition for inhibiting the production and release of slow reacting substance of anaphylaxis (SRS-A) comprising a pharmaceutically effective amount of the compound of claim 2 and a pharmaceutically acceptable carrier.

9. A pharmaceutical composition for inhibiting the production and release of slow reacting substance of anaphylaxis (SRS-A) comprising a pharmaceutically effective amount of the compound of claim 3 and a pharmaceutically acceptable carrier.

10. A pharmaceutical composition for inhibiting the production and release of slow reacting substance of anaphylaxis (SRS-A) comprising a pharmaceutically effective amount of the compound of claim 4 and a pharmaceutically acceptable carrier.

11. A pharmaceutical composition for inhibiting the production and release of slow reacting substance of anaphylaxis (SRS-A) comprising a pharmaceutically effective amount of the compound of claim 5 and a pharmaceutically acceptable carrier.

12. A pharmaceutical composition for inhibiting the production and release of slow reacting substance of anaphylaxis (SRS-A) comprising a pharmaceutically effective amount of the compound of claim 6 and a pharmaceutically acceptable carrier.

13. The composition of claim 7 wherein said pharmaceutically effective amount is in the range of about 0.03 to 250 mg.

14. A method of preventing and/or treating disorders of various allergic diseases, ischemic heat diseases or inflamations, caused by slow reacting substance of anaphylaxis (SRS-A) or leukotriens comprising administering a pharmaceutically effective amount of the composition of claim 7.

15. A method of preventing and/or treating disorders of various allergic diseases, ischemic heat diseases or inflamations, caused by SRS-A or leukotriens comprising administering a pharmaceutically effective amount of the composition of claim 8.

16. A method of preventing and/or treating disorders of various allergic diseases, ischemic heat diseases or inflamations, caused by SRS-A or leukotriens comprising administering a pharmaceutically effective amount of the composition of claim 9.

17. A method of preventing and/or treating disorders of various allergic diseases, ischemic heat diseases or inflamations, caused by SRS-A or leukotriens comprising administering a pharmaceutically effective amount of the composition of claim 10.

18. A method of preventing and/or treating disorders of various allergic diseases, ischemic heat diseases or inflamations, caused by SRS-A or leukotriens comprising administering the composition of claim 11.

19. A method of preventing and/or treating disorders of various allergic diseases, ischemic heat diseases or inflamations, caused by SRS-A or leukotriens comprising administering the composition of claim 12.

* * * * *

UNITED STATES PATENT AND TRADEMARK OFFICE
CERTIFICATE OF CORRECTION

PATENT NO. : 4,618,627
DATED : October 21, 1986
INVENTOR(S) : Kiyoshi Murase et al.

It is certified that error appears in the above-identified patent and that said Letters Patent is hereby corrected as shown below:

On title page the Serial No. should read --609,146--

Signed and Sealed this

Thirty-first Day of March, 1987

Attest:

DONALD J. QUIGG

*Attesting Officer*    *Commissioner of Patents and Trademarks*